(12) United States Patent
Yamaguchi et al.

(10) Patent No.: US 9,044,163 B2
(45) Date of Patent: Jun. 2, 2015

(54) ENDOSCOPE APPARATUS

(75) Inventors: Hiroshi Yamaguchi, Kanagawa (JP);
Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 674 days.

(21) Appl. No.: 13/306,135

(22) Filed: Nov. 29, 2011

(65) Prior Publication Data
US 2012/0154567 A1  Jun. 21, 2012

(30) Foreign Application Priority Data
Dec. 17, 2010  (JP) .................................. 2010-281704

(51) Int. Cl.
*H04N 7/18*  (2006.01)
*A61B 5/1455*  (2006.01)
*A61B 5/1459*  (2006.01)
*A61B 1/00*  (2006.01)
*A61B 1/06*  (2006.01)

(52) U.S. Cl.
CPC .............. *A61B 1/0653* (2013.01); *A61B 1/0638* (2013.01); *A61B 5/14551* (2013.01); *A61B 5/1459* (2013.01); *A61B 1/00009* (2013.01); *A61B 1/063* (2013.01)

(58) Field of Classification Search
CPC ............ A61B 1/05; A61B 1/042; A61B 1/04; A61B 1/041; H04N 2005/2255; H04N 5/2354; H04N 5/2256
USPC .......................................................... 348/68
See application file for complete search history.

(56) References Cited

U.S. PATENT DOCUMENTS

| 5,001,556 | A  | * | 3/1991 | Nakamura et al. ............... 348/70 |
| 5,187,572 | A  | * | 2/1993 | Nakamura et al. ............... 348/68 |
| 7,393,321 | B2 | * | 7/2008 | Doguchi et al. ............... 600/109 |
| 7,479,990 | B2 | * | 1/2009 | Imaizumi et al. .......... 348/223.1 |

(Continued)

FOREIGN PATENT DOCUMENTS

| EP | 1 491 132 A1 | 12/2004 |
| EP | 2 020 202 A2 | 2/2009 |

(Continued)

OTHER PUBLICATIONS

Japanese Office Action for Japanese Application No. 2010-281704, dated Jun. 4, 2013 with partial English translation.

(Continued)

*Primary Examiner* — Sath V Perungavoor
*Assistant Examiner* — Howard D Brown, Jr.
(74) *Attorney, Agent, or Firm* — Birch, Stewart, Kolasch & Birch, LLP

(57) ABSTRACT

The endoscope apparatus includes an illumination unit for irradiating at least three kinds of illumination light having different wavelengths including standard light, first and second reference light onto a biological object, a switching unit for periodically switching the illumination light, an imaging unit for capturing image data by the illumination light in each imaging frame, and an acquisition unit for acquiring biological function information from the captured image data. The irradiation order of illumination light is switched at least in order of the first reference light, the standard light and the second reference light, a standard image by the standard light and reference images by the reference light are acquired, and the biological function information is calculated based on the standard image and the reference images.

16 Claims, 12 Drawing Sheets

(56) References Cited

U.S. PATENT DOCUMENTS

| | | | |
|---|---|---|---|
| 8,231,526 B2* | 7/2012 | Yabe et al. | 600/160 |
| 8,734,333 B2* | 5/2014 | Murakami | 600/160 |
| 2002/0138008 A1* | 9/2002 | Tsujita et al. | 600/473 |
| 2004/0148141 A1* | 7/2004 | Tsujita et al. | 702/190 |
| 2009/0225156 A1* | 9/2009 | Akiyama et al. | 348/68 |
| 2009/0289200 A1* | 11/2009 | Ishii | 250/459.1 |
| 2010/0094136 A1* | 4/2010 | Nakaoka et al. | 600/477 |
| 2011/0301443 A1* | 12/2011 | Yamaguchi et al. | 600/324 |
| 2011/0319711 A1* | 12/2011 | Yamaguchi et al. | 600/109 |

FOREIGN PATENT DOCUMENTS

| | | |
|---|---|---|
| EP | 2 229 870 A1 | 9/2010 |
| JP | 2000-262459 A | 9/2000 |
| JP | 2007-111151 A | 5/2007 |
| JP | 2008-161550 A | 7/2008 |
| JP | 2009-279172 A | 12/2009 |

OTHER PUBLICATIONS

Extended European Search Report dated May 23, 2012 in appiication No. 11190669.9.

* cited by examiner

ENDOSCOPE APPARATUS

BACKGROUND OF THE INVENTION

The present invention relates to an endoscope apparatus capable of calculating biological function information, such as the oxygen saturation of a biological mucosa, with high precision while reducing an influence of the motion of a subject.

In diagnostic imaging using an endoscope, detailed observation or detailed diagnosis is performed in which each site in a wide range of a body cavity is screened by normal light observation using normal white illumination light to find a site suspected of abnormality, the site suspected of abnormality is then observed/examined accurately, precisely, and in detail, and cancer in the body cavity, particularly, the focus site of early-stage cancer, a lesion site, or an abnormal site, such as a hemorrhage, is diagnosed.

In detailed observation/diagnosis (hereinafter, collectively called diagnosis) using the endoscope, when the site suspected of abnormality found in screening is approached, it is necessary to accurately determine whether or not the relevant site is an abnormal site, such as cancer. For this reason, as diagnostic images, it is necessary to observe and diagnose the relevant site in a close contact or enlarged state, or to perceive biological changes in a plurality of features of the relevant site, and there is demand for obtaining a plurality of images using light having various wavelengths.

For this reason, detailed diagnosis is generally performed by special light observation of an enlarged target site. As special light observation, the following observation is performed: narrowband light observation in which light (narrowband light) in a narrow wavelength band having a specific center wavelength is irradiated onto the mucosal tissue of the biological object using the fact that the invasion depth of light in the depth direction with respect to the biological tissue depends on the wavelength of light, and tissue information at a desired depth of a biological tissue, particularly, form information of a blood vessel at a predetermined depth (surface layer blood vessel (blue: B), intermediate layer blood vessel (green: G), deep layer blood vessel (red: R), or the like) are obtained to diagnose the presence/absence of a focus, such as a cancer tissue; narrowband light observation in which narrowband light in the B region is irradiated onto a biological tissue using the absorbance of hemoglobin and the oxygen saturation in the blood is measured; infrared light observation in which near-infrared light is irradiated onto a biological tissue using the absorbance of hemoglobin or the absorbance of ICG (indocyanine green) to be bound to protein and the oxygen saturation in the blood is measured to image a blood vessel; or fluorescent observation in which the presence/absence of a focus, such as cancer cells, is determined using autogenous fluorescence generated from a biological tissue, onto which excitation light in a specific narrow wavelength band is irradiated or fluorescence generated from a fluorescent medication dispersed in a specific focus, such as cancer cells, in a biological tissue.

For example, Patent Document 1 describes an endoscope system which has three observation modes including a normal light observation mode in which a reflected light image is presented, a screening fluorescent observation mode (first fluorescent observation mode) in which a fluorescence intensity image is presented, and unmixing fluorescent observation mode (second fluorescent observation mode) in which the concentration distribution of a fluorescent medication obtained by computation from a fluorescence intensity image is presented, and can select a suitable observation mode by a mode selector.

In this endoscope system, a white light source, such as a xenon lamp, a light source for illumination light constituted by a switching RGB color filter, and two excitation light sources constituted by semiconductor lasers which emit excitation light having different wavelengths with the peak wavelengths of 680 nm and 700 nm are used as light sources. While the insertion portion at the tip of the endoscope is inserted into a body cavity and then reaches an observation site, imaging is done in the normal light observation mode using the light source for illumination light, that is, normal screening is performed. In this mode, the two excitation light sources are turned off. If the insertion portion at the tip of the endoscope reaches the observation site, the observation mode is switched to the screening fluorescent observation mode, such that the observation-target site is cleaned and two fluorescent probes are dispersed.

In the screening fluorescent observation mode, the light source for illumination light and one excitation light source are used. When the light source for illumination light is turned on, only B illumination light is irradiated onto the observation site, and imaged as a reflected light image (B) by an image pickup device. When the excitation light source is turned on, two kinds of fluorescence which are generated when the two fluorescent probes dispersed in the observation site are excited by emitted excitation light are imaged as fluorescent images by an image pickup device including an excitation light cut filter, and are displayed on a display unit as an image in which a fluorescent image and a reflected light image overlay each other. If fluorescence is generated, the observation mode is switched to the unmixing observation mode. When fluorescence is not generated, the observation mode is switched to the normal observation mode, moving to the next observation site.

In the unmixing observation mode, the light source for illumination light and the two excitation light sources are used. In the same manner as described above, two kinds of fluorescent images in which a reflected light image and two kinds of fluorescence are color-mixed are acquired, concentration information of the fluorescent probes is calculated from the two kinds of fluorescent images, and overlaid on the reflected light image to be displayed on the display unit. It is possible to determine the presence/absence of a cancer cell on the basis of the concentration information with the two kinds of fluorescence.

[Patent Document 1] JP 2008-161550 A

SUMMARY OF THE INVENTION

On the other hand, in the endoscope system described in Patent Document 1, screening by fluorescent observation is performed, and the concentration of the fluorescent medication of the observation-target site by fluorescent observation in a fluorescence-generated site found by screening in the unmixing observation mode is visualized, thereby performing detailed diagnosis. Detailed observation in the unmixing observation mode simply means that the light source for illumination light and the first and second excitation light sources are switched sequentially to acquire B reflected light image information, first fluorescent image information, and second fluorescent image information, and the concentration information is computed using the first and second fluorescent image information to perform fluorescent observation.

For this reason, when another special light observation, for example, narrowband light observation for calculating biological function information, such as blood vessel depth information, blood volume information, or oxygen saturation information is combined with fluorescent observation, it is necessary to irradiate more narrowband light. Accordingly, the calculation of the biological function information is likely to be influenced by the motion of the subject, making it impossible to obtain accurate biological function information.

An object of the invention is to provide an endoscope apparatus capable of computing biological function information, such as the oxygen saturation of a biological mucosa, on the basis of spectral images obtained by sequentially switching and irradiating illumination light having a plurality of wavelengths accurately and with high precision while reducing the influence of the motion of a subject, calculating high-precision biological function information, visualizing a biological function, such as oxygen saturation, accurately and with high precision, and obtaining a diagnostic image for high-precision detailed diagnosis.

To achieve the above objects, the present invention provides an endoscope apparatus comprising illumination means for irradiating at least three kinds of illumination light having different wavelengths including standard light, first reference light, and second reference light onto a biological object serving as a subject; illumination light switching means for periodically switching the at least three kinds of illumination light irradiated by the illumination means in each imaging frame; imaging means for receiving return light from the subject onto which the at least three kinds of illumination light switched by the illumination light switching means are irradiated and capturing image data in each imaging frame; and biological information acquisition means for acquiring biological function information relating to the biological object from the captured image data captured by the imaging means, wherein the illumination light switching means switches an irradiation order of the at least three kinds of illumination light by the illumination means at least in order of the first reference light, the standard light, and the second reference light, the standard light is irradiated onto the biological object by the illumination means to acquire a standard image by the imaging means, and at least two kinds of illumination light including the first and second reference light other than the standard light is irradiated onto the biological object by the illumination means to acquire reference images by the imaging means, and the biological information acquisition means calculates the biological function information based on the standard image and the reference images acquired by the imaging means.

Preferably, the standard light is broadband light including a visible light wavelength band, and the first and second reference light are narrowband light having a predetermined wavelength bandwidth, the imaging means is an RGB color image sensor, and the biological information acquisition means performs a spectral estimation process from captured image data obtained by irradiation of the broadband light, obtains, as the standard image, a first standard wavelength image for comparison with a first reference image by the first reference light and a second standard wavelength image for comparison with a second reference image by the second reference light, and calculates the biological function information based on the first reference image and the first standard wavelength image, and/or the second reference image and the second standard wavelength image.

Preferably, the broadband light is pseudo white light including excitation light which is narrowband light having a predetermined wavelength and fluorescence which is generated from a fluorescent substance excited by the excitation light, a wavelength of the excitation light falls between a wavelength of the first reference light and a wavelength of the second reference light.

Preferably, the illumination means includes three narrowband light sources which respectively emit the excitation light, the first reference light, and the second reference light, and a narrowband light source which emits the excitation light and the fluorescent substance constitute a broadband light source which emits the broadband light.

Preferably, each of the standard light, the first reference light, and the second reference light is narrowband light having a predetermined wavelength bandwidth, and a wavelength of the standard light falls between a wavelength of the first reference light and a wavelength of the second reference light, and the biological information acquisition means calculates the biological function information based on the standard image by the standard light, the first reference image by the first reference light, and the second reference image by the second reference light.

Preferably, the illumination means further includes a broadband light source which emits broadband light including a visible wavelength band, in addition to three narrowband light sources which respectively emit the standard light, the first reference light, and the second reference light.

Preferably, the endoscope apparatus further comprises display means for displaying the biological function information and normal observed image acquisition means for irradiating the broadband light emitted from the broadband light source onto the biological object to acquire a normal observed image by the imaging means, wherein the display means displays a biological function information image in which the biological function information calculated by the biological information acquisition means is overlaid on the normal observed image acquired by the normal observed image acquisition means.

Preferably, the narrowband light source which emits narrowband light as the standard light or the excitation light is a first blue laser which emits narrowband light having a wavelength in a blue region, the narrowband light source which emits narrowband light as the first reference light is a second blue laser which emits narrowband light in a wavelength band from the blue region to a blue-green region longer than the emission wavelength band of the first blue laser, and the narrowband light source which emits narrowband light as the first reference light is a third blue laser which emits narrowband light in a wavelength band from a blue-violet region to a blue region having a wavelength shorter than the emission wavelength band of the first blue laser.

Preferably, the wavelength band of narrowband light as the standard light or the excitation light is 440±10 nm, the wavelength band of narrowband light as the first reference light is 470±10 nm, and the wavelength band of narrowband light as the second reference light is 400±10 nm.

Preferably, the biological function information is information relating to components of the biological object and a structure of the biological object, and the biological information acquisition means separates and images information relating to the components of the biological object and information relating to the structure of the biological object based on a first feature quantity obtained by comparing a first reference image by the first reference light with the standard image by the standard light and a second feature quantity obtained by comparing a second reference image by the second reference light with the standard image.

Preferably, the first reference light is narrowband light having a wavelength suitable for acquiring oxygen saturation of blood of the biological object as information relating to the components of the biological object, and the second reference light is narrowband light having a wavelength suitable for acquiring information of a surface layer blood vessel of the biological object as information relating to the structure of the biological object.

Preferably, the biological information acquisition means computes oxygen saturation of blood of the biological object as information relating to components of the biological object and computes blood vessel depth and/or blood volume of the biological object as information relating to structure of the biological object.

Preferably, the imaging means is a color image pickup device capable of separately imaging at least three wavelength bands.

Preferably, the standard light and the first and second reference light are emitted from different illumination openings at a tip of the endoscope and illuminate the biological object.

According to the invention, when sequentially switching and irradiating illumination light having a plurality of different wavelengths, the irradiation order of illumination light having a plurality of wavelengths is set to irradiate illumination light having wavelengths before and after the wavelength of illumination light as the standard for computation of spectral images such that computation of spectral images of different wavelength components is unlikely to be influenced by the motion of the subject. Therefore, it is possible to compute the biological function information, such as the oxygen saturation based on the spectral images of different wavelength components accurately and with high precision while reducing the influence of the motion of the subject.

Therefore, according to the invention, it is possible to calculate the biological function information accurately and with high precision without reducing the influence of the motion of the subject, to visualize a biological function, such as oxygen saturation, accurately and with high precision, and to obtain a diagnostic image for high-precision detailed diagnosis.

An object of the invention is to provide an endoscope apparatus capable of computing biological function information, such as the oxygen saturation of a biological mucosa, on the basis of spectral images obtained by sequentially switching and irradiating illumination light having a plurality of wavelengths accurately and with high precision while reducing the influence of the motion of a subject, calculating high-precision biological function information, visualizing a biological function, such as oxygen saturation, and obtaining a diagnostic image for high-precision detailed diagnosis.

An object of the invention is to provide an endoscope apparatus capable of computing biological function information, such as the oxygen saturation of a biological mucosa, on the basis of spectral images obtained by sequentially switching and irradiating illumination light having a plurality of wavelengths accurately and with high precision while reducing the influence of the motion of a subject, calculating high-precision biological function information, visualizing a biological function, such as oxygen saturation, and obtaining a diagnostic image for high-precision detailed diagnosis.

DETAILED DESCRIPTION OF THE INVENTION

Hereinafter, an endoscope apparatus according to the invention will be described with reference to a preferred embodiment shown in the accompanying drawings.

Figure 1:
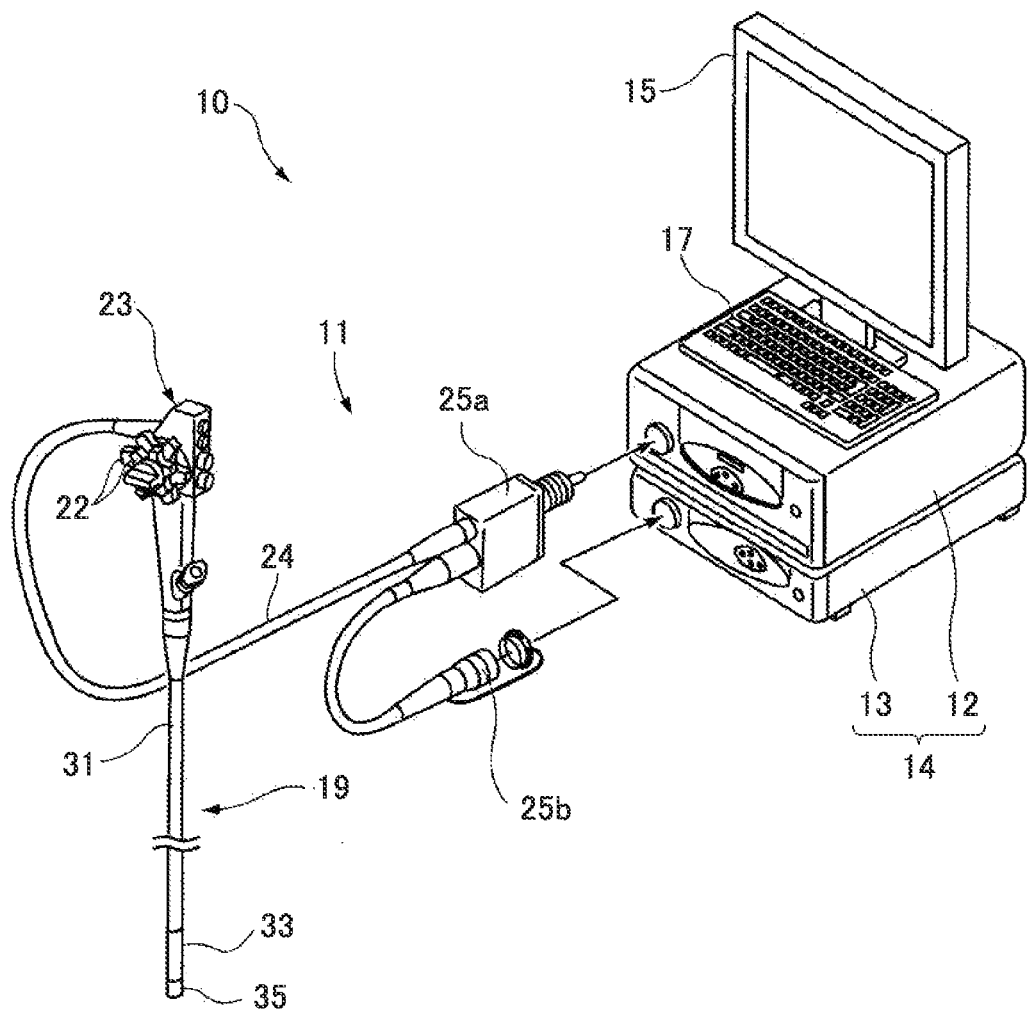
FIG. 1 is a perspective view showing the appearance of an example of an endoscope apparatus according to an embodiment of the invention.
Figure 2:
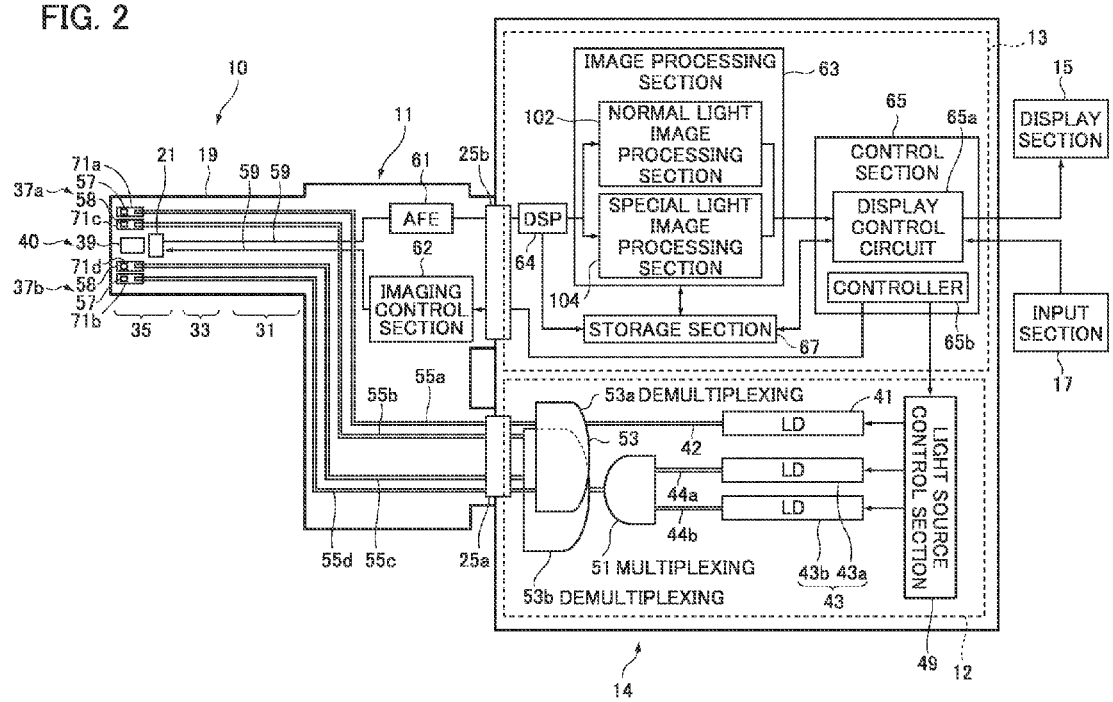
FIG. 2 is a schematic view conceptually showing the overall configuration of an example of the endoscope apparatus shown in FIG. 1.

FIG. 1 is a perspective view showing the appearance of an example of an endoscope apparatus according to an embodiment of the invention. FIG. 2 is a schematic view conceptually showing the overall configuration of the endoscope apparatus shown in FIG. 1.

As shown in FIGS. 1 and 2, an endoscope apparatus 10 of the invention is one type of medical instrument. The endoscope apparatus 10 includes an endoscope 11 which images the inside of a body cavity of a subject, a light source device 12 which supplies light to be irradiated into body cavity for imaging, a processor 13 which generates image information of an image including biological information, such as blood vessel information of a subject tissue inside the body cavity, on the basis of an image signal obtained by imaging, a control device 14 to which the endoscope 11 is connected, a display section 15 which is constituted by a monitor for displaying image information, such as an image inside the body cavity, and an input section 17 which receives an input operation of the endoscope apparatus 10.

The endoscope apparatus 10 of the invention includes observation modes of a normal observation mode (also referred to as a normal light mode), a special light observation mode (also referred to as a special light mode), and the like.

Hereinafter, although narrowband light observation in which the oxygen saturation of blood of a biological object, particularly, surface layer and intermediate-to-deep layer oxygen saturation, blood vessel depth information, blood volume information, and the like are acquired as the biological information of the subject in a special light observation mode will be described as a representative example, the invention is not limited thereto. Narrowband light observation in which blood vessel size information, blood vessel set information, blood vessel shape information, blood volume information, and the like are acquired may be used. It should be noted that, in the special light mode, not only narrowband light observation, but also special observation, such as infrared light observation, autogenous fluorescent observation, or fluorescent observation, may be performed.

First, the endoscope 11 of this example will be described.

The endoscope 11 is an electronic endoscope having an illumination optical system which emits illumination light from the tip of the insertion portion 19 inserted into the subject, and an imaging optical system which includes an image pickup device 21 (see FIG. 2) imaging a region to be observed. The endoscope 11 is optically connected to the light source device 12 and electrically connected to the processor 13. The processor 13 is electrically connected to the display section 15 and the input section 17. The input section 17 functions as a UI (user interface) which receives an input operation, such as the setting of the observation mode of the normal light mode or the special light mode or function setting.

The endoscope apparatus 10 of the invention may have a recording section (recording device) (not shown) which outputs image information or the like as a hard copy image, in addition to the display section 15.

The endoscope 11 includes a flexible insertion portion 19 which is inserted into the body cavity, an operation section 23 which is provided in the base portion of the insertion portion 19 and performs a bending operation of the tip of the insertion portion 19 or an operation for observation, a universal cord 24 which connects the operation section 17 and the control device 14, and connector portions 25a and 25b which are attached to the universal cord 24 and detachably connects the endoscope 11 to the control device 14. Though not shown, inside the operation section 23 and the insertion portion 19, various channels including a forceps channel into which a treatment tool for tissue extraction or the like is inserted, a channel for air supply/water supply, and the like are provided.

The insertion portion 19 is constituted by a flexible portion 31, a bent portion 33, and a tip portion 35. As shown in FIG. 2, the tip portion 35 has arranged therein irradiation openings 37a and 37b which irradiate illumination light by the illumination optical system onto a region to be observed, an image pickup device 21 which acquires image information of the region to be observed, and an objective lens unit 39 which constitutes an imaging optical system in the light-receiving surface of the image pickup device 21. The outer surface of the objective lens unit 39 constitutes an observation window 40.

The bent portion 33 is provided between the flexible portion 31 and the tip portion 35, and is bendable by a rotation operation of an angle knob 22 arranged in the operation section 23 shown in FIG. 1. The bent portion 33 can be bent in an arbitrary direction at an arbitrary angle in accordance with a site or the like of the subject in which the endoscope 11 is used, such that the irradiation openings 37a and 37b of the endoscope tip portion 35 and the observation direction of the image pickup device 21 can be directed to a desired observation site.

The structure of the illumination optical system inside the endoscope 11, the electrical configuration of the imaging system, and the structure of the irradiation openings 37a and 37b of the insertion portion 19 will be described below in detail.

Next, the light source device 12 and the processor 13 in the control device 14 of this example will be described.

In the invention, the light source device 12 generates illumination light which is supplied to the irradiation openings 37a and 37b of the tip portion 35 of the endoscope 11. The processor 13 performs an image process on a captured image signal to be transmitted from the image pickup device 21 of the endoscope 11 on the basis of an instruction from the operation section 23 or the input section 17 of the endoscope 11 to generate an image for display and supplies the image for display to the display section 15.

The light source device 12 has a normal light source section 41 which emits illumination light including only broadband light, a narrowband light source section 43 which emits illumination light including only a plurality of narrowband light, and a light source control section 49 which switches the emission of broadband light of the normal light source section 41 and each narrowband light source of the narrowband light source section 43 on the basis of an instruction according to each observation mode from a control section 65 of the narrowband light source processor 13 in accordance with each observation mode, and individually controls the emission amount.

In the example of the drawing, the normal light source section 41 includes a broadband light source having a narrowband light source 41a which emits excitation light E as narrowband light N1 having a predetermined narrowband wavelength, and a fluorescent substance 57 which emits fluorescence by the irradiation of excitation light E.

That is, the combination of the narrowband light source 41a and the fluorescent substance 57 become a broadband light source which emits broadband light, such as white light, constituted by excitation light and fluorescence. In the broadband light source, when excitation light E emitted from the narrowband light source 41a is irradiated onto the fluorescent substance 57, the fluorescent substance 57 is excited by excitation light E to emit fluorescent having at least a wavelength band other than the wavelength band of excitation light E, excitation light E is transmitted, and combined light of emitted fluorescence and transmitted excitation light E is emitted as pseudo white light.

In the configuration example of this embodiment, the narrowband light source 41a excites the fluorescent substance 57 to emit fluorescence, and constitutes a broadband light source, called Micro-White (Product Name). It is preferable that the narrowband light source 41a emits blue laser light (narrowband light N1) having a limited wavelength of 440±10 nm as excitation light E, and is an LD (laser diode) having a center emission wavelength of 445 nm.

The narrowband light source section 43 has a plurality of narrowband light sources having different emission wavelengths. In the example of the drawing, the narrowband light source section 43 has a narrowband light source 43a which emits narrowband light N2 having a predetermined narrowband wavelength, and a narrowband light source 43b which emits narrowband light N3 having an emission wavelength different from narrowband light N2. That is, in the example of the drawing, second illumination light emitted from the narrowband light source section 43 includes only narrowband light N2 and N3.

In the configuration diagram of this embodiment, the narrowband light source 43a is a light source which is suitable for observation of a surface layer blood vessel. It is preferable that the narrowband light source 43a emits blue-violet laser light (narrowband light N2) having a limited wavelength of 400±10 nm, preferably, 405 nm, and is an LD having a center emission wavelength of 405 nm.

Similarly to the narrowband light source 41b, the narrowband light source 43b is a light source which is suitable for calculating the oxygen saturation in the blood. It is preferable that the narrowband light source 43b emits blue-green laser light (narrowband light N3) having a limited wavelength of 470±10 nm, preferably, 473 nm, and is an LD having a center emission wavelength of 473 nm.

For the narrowband light sources 41a, 43a, and 43b, for example, a GaN-based semiconductor laser (laser diode), a broad-area InGaN-based laser diode, an InGaNAs-based laser diode, a GaNAs-based laser diode, and the like may be used. As the above-described light sources, a configuration using a light-emitting substance, such as a light-emitting diode, may be made.

The light source control section 49 of the light source device 12 switches the emission of the narrowband light sources 41a, 43a, and 43b and controls the emission amount in accordance with each observation mode. That is, the narrowband light sources 41a, 43a, and 43b are individually subjected to dimming control by the light source control section 49, and the light amount ratio is variable. According to the invention, that is, in the special light observation mode of the invention, the emission timing of the narrowband light sources is in order of the narrowband light sources 43a, 41a, and 43b.

First, when the observation mode is the normal light mode, the light source control section 49 performs controls such that only the narrowband light source 41a of the normal light source section 41 is turned on, and the narrowband light sources 43a and 43b of the narrowband light source section 43 are turned off. That is, in the normal light mode, the narrowband light source 41a of the normal light source section 41 is turned on on the basis of a control signal from the light source control section 49, and broadband light which is constituted by pseudo white light obtained by synthesizing excitation light E and fluorescence from the fluorescent substance 57 is emitted from the normal light source section 41 as illumination light.

When the observation mode is the special light mode, the light source control section 49 performs control such that the narrowband light source 41a of the normal light source section 41 and the narrowband light sources 43a and 43b of the narrowband light source section 43 are turned on. That is, in the special light mode, the narrowband light source 43a of the narrowband light source section 43, the narrowband light source 41a of the normal light source section 41, and the narrowband light source 43b of the narrowband light source section 43 are turned on in that order on the basis of a control signal from the light source control section 49. Narrowband light N2 from the narrowband light source section 43, broadband light from the normal light source section 41, and narrowband light N3 from the narrowband light source section 43 are emitted in that order as illumination light (see FIG. 15).

Excitation light E (narrowband light N1) emitted from the narrowband light sources 41a and 41b of the normal light source section 41 is input to an optical fiber 42 by a condensing lens (not shown), and transmitted to the connector portion 25a through a coupler 53a (53) serving as a demultiplexer.

Narrowband light N2 and N3 emitted from the narrowband light sources 43a and 43b of the narrowband light source section 43 are respectively input to optical fibers 44a and 44b by a condensing lens (not shown), and transmitted to the connector portion 25a through a combiner 51 serving as a multiplexer and a coupler 53b (53) serving as a demultiplexer. The invention is not limited thereto, and narrowband light N1 (excitation light E), N2, and N3 may be multiplexed by the combiner 51, or may be guided to the coupler 53b and multiplexed without using the combiner 51. A configuration may be made in which narrowband light N1 to N3 from the narrowband light sources 41a, 43a, and 43b are directly transmitted to the connector portion 25a using one coupler without using at least one of the two couplers 53 (53a and 53b) or without using at least one of the combiner and the coupler.

Next, the configuration of the illumination optical system of the endoscope 11 optically connected to the light source device 12 and the electrical configuration of an imaging system which is connected to the processor 13 will be described.

The illumination optical system of the endoscope 11 includes optical fibers 55a to 55d, fluorescent substances 57 which are arranged at the tip of the optical fibers 55a and 55d and constitute the broadband light sources of the normal light source section 41, and optical deflection/diffusion members 58 which are arranged at the tip of the optical fibers 55b and 55c.

The optical fibers 55a to 55d constituting the illumination optical system are multi-mode fibers. For example, a thin fiber cable having a core diameter of 105 μm, a cladding diameter of 125 μm, and a diameter including a protective layer as an outer layer of ϕ0.3 to 0.5 mm can be used.

Narrowband light N1 from the narrowband light source 41a of the normal light source section 41 is introduced to the optical fibers 55a and 55d extended from the connector portion 25a to the tip portion 35 at an arbitrary timing, and becomes white illumination light through the fluorescent substances 57 serving as wavelength conversion members arranged in the tip portion 35.

Narrowband light N2 and N3 from the narrowband light sources 43a and 43b of the narrowband light source section 43 are respectively introduced to the optical fibers 55b and 55c extended from the connector portion 25a to the tip portion 35 at an arbitrary timing, and become illumination light through the optical deflection/diffusion members 58 arranged in the tip portion 35.

The combination of the optical fiber 55a and the fluorescent substance 57 constitutes a projection unit 71a, and the combination of the optical fiber 55b and the optical deflection/diffusion member 58 constitutes a projection unit 71c. The combination of the optical fiber 55c and the optical deflection/diffusion member 58 constitutes a projection unit 71d, and the combination of the optical fiber 55d and the fluorescent substance 57 constitutes a projection unit 71b. A pair of projection units 71a and 71c and a pair of projection units 71b and 71d are arranged on both sides with the image pickup device 21 and the objective lens unit 39 of the tip portion 35 of the endoscope 11 sandwiched therebetween.

Figure 3A:
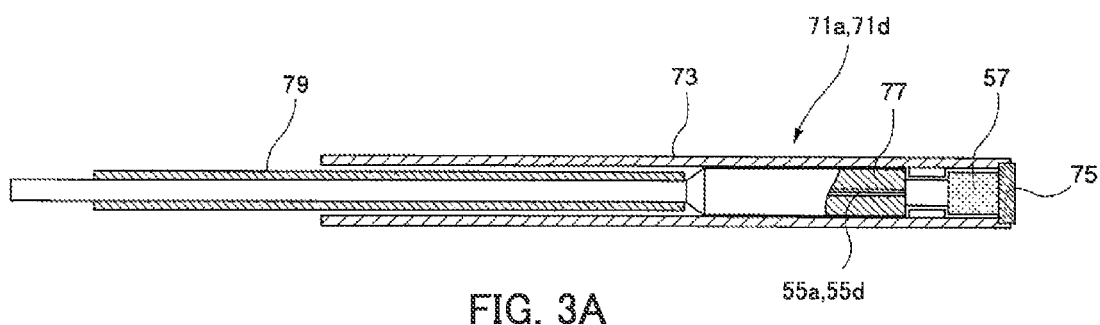
FIGS. 3A and 3B are sectional configuration diagrams of a projection unit including a fluorescent substance of a tip portion of an endoscope in the endoscope apparatus shown in FIG. 1, and a projection unit including an optical deflection/diffusion member.
Figure 3B:
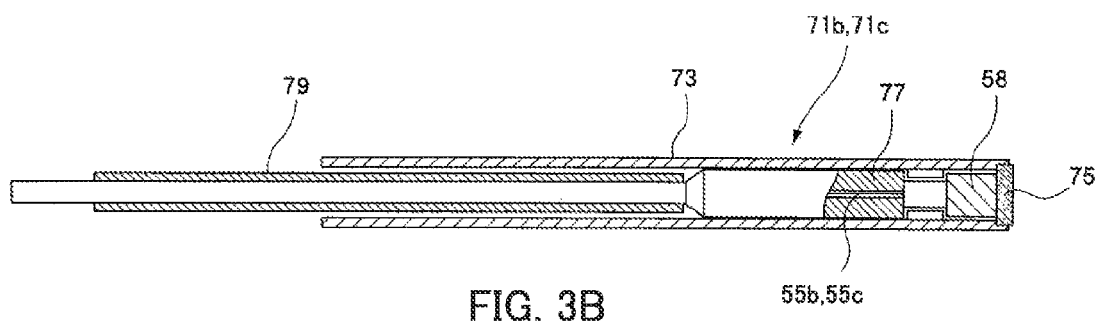

FIG. 3A is a sectional configuration diagram of the projection units 71a and 71d, and FIG. 3B is a sectional configuration diagram of the projection units 71b and 71c.

As shown in FIG. 3A, the projection unit 71a and the projection unit 71d have the same configuration, and respectively include a fluorescent substance 57, a cylindrical sleeve member 73 which covers the circumference of the fluorescent substance 57, a protective glass (illumination window) 75 which seals one end of the sleeve member 73, and a ferrule 77 which is inserted into the sleeve member 73 and holds the optical fiber 55a (55d) on the center axis. A flexible sleeve 79 is inserted between the optical fiber 55a (55d) extended from the rear end of the ferrule 77 and the sleeve member 73 so as to cover the outer layer of the optical fiber 55a (55d).

The projection unit 71b and the projection unit 71c have the same configuration, and have the same configuration as the projection units 71a and 71d except that, instead of the fluorescent substances 57 of the projection units 71a and 71d, the optical deflection/diffusion members 58 are arranged, and light is guided from the optical fibers 55b and 55c.

The fluorescent substances 57 of the projection units 71a and 71d include a plurality of fluorescent substance materials (for example, YAG-based fluorescent substances or fluorescent substances, such as BAM ($BaMgAl_{10}O_{17}$)) which absorb a part of blue laser light (excitation light E) from the narrowband light source 41a, and generate green to yellow excited luminescence light. Thus, green to yellow excited luminescence light excited by blue laser light and blue laser light transmitted by the fluorescent substance 57 without thereby being absorbed are combined to generate white (pseudo white) illumination light.

The fluorescent substance 57 can prevent the occurrence of superimposition of noise causing imaging failure or flickering at the time of motion image display caused by a spectrum due to the coherence of laser light. It is preferable that the fluorescent substance 57 is made of a material, in which a fluorescent material and a filler have a particle size such that a small amount of infrared light is absorbed and a large amount of infrared light is scattered, taking into consideration the difference in refractive index between a fluorescent material constituting the fluorescent substance and resin for fixing/solidification. Thus, the scattering effect increases without lowering the light intensity with respect to red or infrared light, and the optical loss decreases.

Figure 4A:
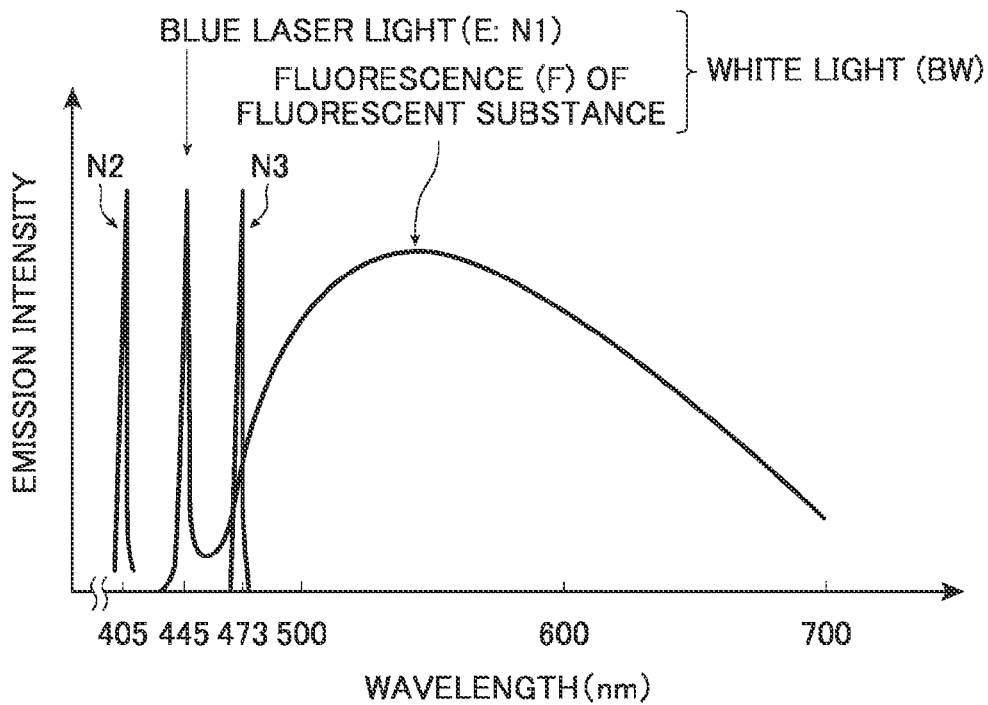
FIG. 4A is a graph showing blue laser light from a narrowband light source for use in the endoscope apparatus shown in FIG. 1, an emission spectrum when blue laser light is wavelength-converted by a fluorescent substance, and an emission spectrum of a laser light from each narrowband light source.

FIG. 4A is a graph showing blue laser light (excitation light E) from the narrowband light source 41a, an emission spectrum F when blue laser light E is wavelength-converted by the fluorescent substance 57, and the emission spectrum of laser light (narrowband light N2 and N3) from the narrowband light sources 43a and 43b.

Blue laser light E from the narrowband light source 41a is expressed by an emission line having a center wavelength of 445 nm, and excited and emitted light F from the fluorescent substance 57 due to blue laser light E from the narrowband light source 41a has a spectral intensity distribution in which emission intensity increases in a wavelength band of about 450 nm to 700 nm. The above-described pseudo white light BW is formed by a profile based on excited and emitted light F and blue laser light E. As in this configuration example, if a semiconductor light-emitting element is used as an excitation light source, high-intensity white light is obtained with high emission efficiency, making it possible to easily adjust the intensity of white light and to suppress changes in the color temperature and chromaticity of white light to be small.

White light used herein is not strictly limited to include all wavelength components of visible light. For example, white light may include light in a specific wavelength band of R (red), G (green), or B (blue) which are standard colors. For example, white light broadly includes light including wavelength components from green to red, light including wavelength components from blue to green, or the like.

Broadband light used herein preferably includes at least light regarded as white light, and may include light in at least one of the near-infrared or infrared wavelength band and the near-ultraviolet or ultraviolet wavelength band.

Meanwhile, narrowband light used herein preferably refers to light which belongs to one of the specific wavelength bands of the standard colors R, G, B, and the like, light having a wavelength band separated from a wavelength band of another narrowband light, or light having a wavelength bandwidth of 20 nm, preferably, ±10 nm with respect to the center wavelength.

Blue-violet laser light N2 from the narrowband light source 43a is expressed by an emission line having a center wavelength of 405 nm, and blue-green laser light N3 from the narrowband light source 43b is expressed by an emission line having a center wavelength of 473 nm.

From above, in this embodiment, a laser light source (LD445) which emits blue laser light E having a center wavelength of 445 nm can be used as the narrowband light source 41a, a laser light source (LD405) which emits blue laser light having a center wavelength of 405 nm can be used as the narrowband light source 43a, and a laser light source (LD473) which emits blue laser light having a center wavelength of 473 nm can be used as the narrowband light source 43b.

The optical deflection/diffusion members 58 of the projection units 71b and 71c may be made of a material which transmits blue-violet laser light N2 and blue-green laser light N3 from the narrowband light sources 43a and 43b. For example, a resin material, glass, or the like having translucency is used. The optical deflection/diffusion member 58 may have a configuration in which an optical diffusion layer with minute concavo-convexes or in which particles (filler or the like) having different reflective indexes are mixed, on the surface of a resin material, glass, or the like is provided or a configuration in which a semitransparent material is used. Thus, transmitted light emitted from the optical deflection/diffusion member 58 becomes illumination light having a narrowband wavelength whose light quantity is uniformized in a predetermined irradiation region.

Next, as shown in FIG. 2, the imaging system of the endoscope 11 has an imaging control section 62 which supplies a driving signal to the image pickup device 21 on the basis of an instruction according to each observation mode from the control section 65, which issues an instruction in accordance with each observation mode to the light source control section 49 of the light source device 12, particularly, according to the special light observation mode, an image pickup device 21 which images a region to be observed of the subject at a predetermined frame rate according to each observation mode on the basis of the driving signal from the imaging control section 62 to acquire image information, and outputs an image signal of the acquired captured image, and an analog processing circuit (AFE (Analog Front End)) 61 which processes an analog image from the image pickup device 21 to a digital image so as to be processed by a digital signal process in the digital signal processing section 64 of the processor 13.

The imaging control section 62 controls the driving of the image pickup device 21 on the basis of an instruction according to each observation mode of the control section 65. Specifically, the imaging control section 62 controls imaging by the image pickup device 21 and the output of a captured image signal from the image pickup device 21 in each imaging frame in accordance with the emission of the narrowband light source 41a of the normal light source section 41 and the narrowband light sources 43a and 43b of the narrowband light source section 43 in the light source device 12 which is controlled in accordance with the observation mode.

The imaging control of the image pickup device 21 by the imaging control section 62, that is, imaging frame control will be described below in detail.

Figure 4B:
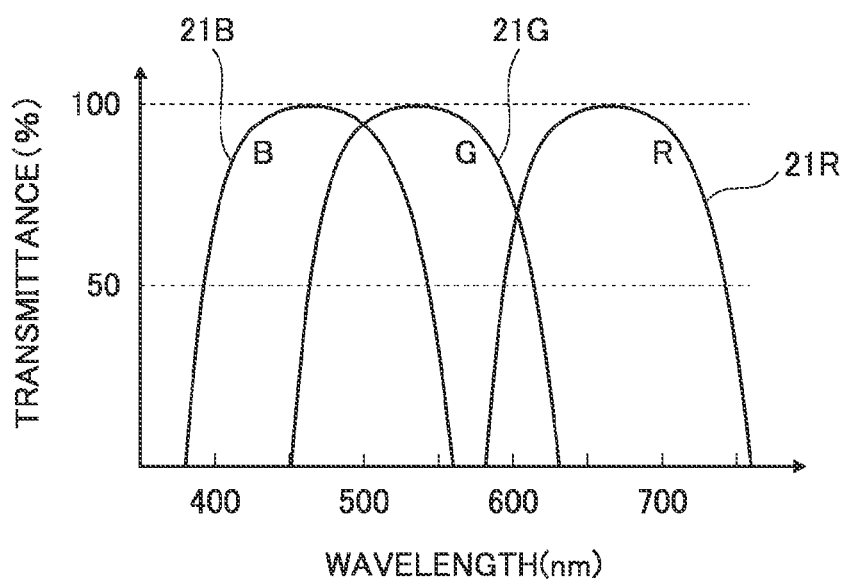
FIG. 4B is a graph showing spectral transmittance of a color filter of an image pickup device for use in the endoscope apparatus shown in FIG. 1.

The image pickup device 21 is constituted by a color image sensor, such as a CCD (Charge Coupled Device) image sensor or a CMOS (Complementary Metal-Oxide Semiconductor) image sensor, which receives return light from the region to be observed and acquires captured image information. The image pickup device 21 is controlled in accordance with each observation mode by the imaging control section 62, and forms the shape of the region to be observed of the subject, onto which the illumination light of the light source device 12 is irradiated, on the light-receiving surface of the image pickup device 21 by the objective lens unit 39 to capture an image in each frame. In this embodiment, the image pickup device 21 is a color CCD image sensor, and on the light-receiving surface of the image pickup device 21, for example, color filters 21R, 21G, and 21B of R, G, and B colors having spectral transmittance shown in FIG. 4B are provided. An R pixel, a G pixel, and a B pixel constitute one set, and a plurality of sets of pixels are arranged in a matrix.

In the special light observation mode, illumination light including pseudo white light resulting from the blue laser light (excitation light) from the narrowband light source 41a of the normal light source section 41 of the light source device 12 and excited luminescence light from the fluorescent substance 57, and narrowband light N2 and N3, which are laser light emitted from the narrowband light sources 43a and 43b, is controlled by the light source control section 49, and irradiated from the tip portion 35 of the endoscope 11 toward the region to be observed of the subject in each imaging frame in the above-described predetermined order.

Thus, the image pickup device 21 images the region to be observed, onto which illumination light from the light source device 12 controlled by the light source control section 49 is irradiated in the above-described predetermined order, in each imaging frame controlled by the imaging control section 62. As a result, the image pickup device 21 is controlled by an imaging control signal which is transmitted from the imaging control section 62 through a scope cable 59 and outputs an image signal of a captured image at a predetermined frame rate.

The image signal of the captured image output from the image pickup device 21 is transmitted to the analog processing circuit (AFE) 61 through the scope cable 59, subjected to various analog signal processes, converted to a digital signal, and input to the processor 13 through the connector portion 25b.

The AFE 61 converts the image obtained by the image pickup device 21 in a digital format while suppressing various kinds of noise at the time of analog-to-digital conversion (A/D) to be the minimum so as to transmit the image to a digital back end, such as the DSP 64, as faithfully as possible.

Though not shown, the AFE 61 includes, for example, a correlated double sampling circuit (CDS), an automatic gain control circuit (AGC), and an analog/digital (A/D) converter. The CDS performs a correlated double sampling process on the captured image signal from the image pickup device (CCD) 21, and eliminates noise due to the driving of the image pickup device 21. The AGC amplifies the captured image signal with noise removed by the CDS. The A/D converter converts the captured image signal amplified by the AGC to a digital captured image signal having a predetermined number of bits and inputs the result to the processor 13.

In the processor 13, various processes are performed on a digital image signal, and image information including biological function information, such as information relating to the components of the biological object, such as the oxygen saturation of blood of the biological object in the region to be observed of the subject, or information relating to the structure of the biological object, such as blood vessel depth and/or blood volume, is generated and displayed on the display section 15 as an endoscope diagnosis/observation image.

The details of the processor 13 will be described below.

Next, the configuration of the tip portion of the endoscope will be described in detail.

Figure 5:
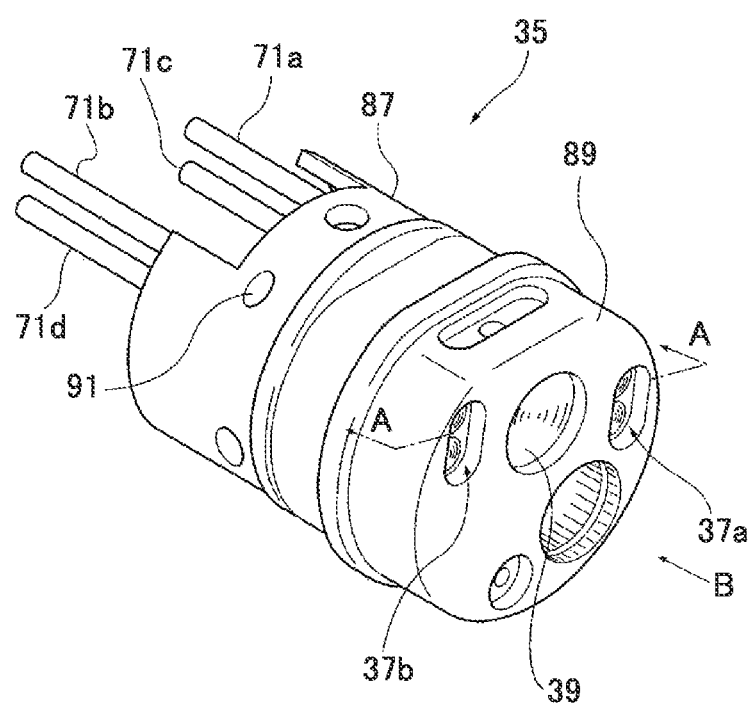
FIG. 5 is a perspective view showing the schematic configuration of an example of a tip portion of an endoscope in the endoscope apparatus shown in FIG. 1.
Figure 6:
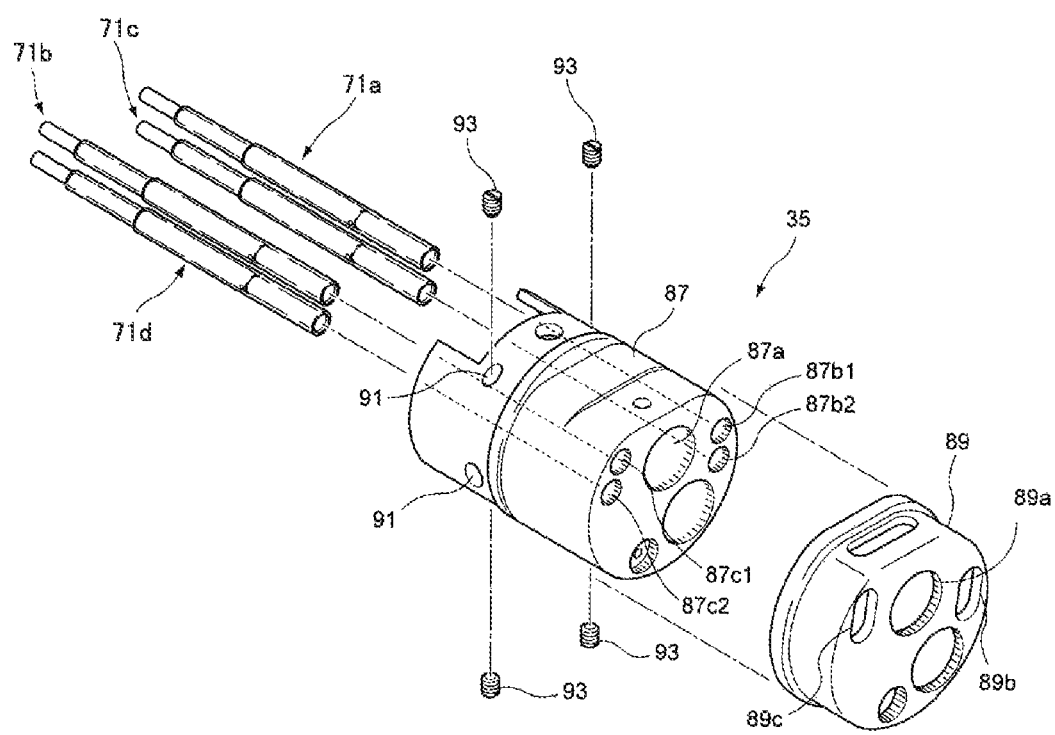
FIG. 6 is an exploded view of the tip portion of the endoscope shown in FIG. 5.

FIG. 5 is a perspective view showing the schematic configuration of the tip portion of the endoscope. FIG. 6 is an exploded view of the tip portion of the endoscope shown in FIG. 5.

As shown in FIGS. 5 and 6, the tip portion 35 of the endoscope 11 is configured such that various components, such as the projection units 71a to 71d, are attached to a hard tip portion 87 which is formed of stainless steel or the like to have a plurality of bores along the longitudinal direction. The hard tip portion 87 has a bore 87a in which the imaging optical system including the image pickup device 21 shown in FIG. 2 is accommodated, and bores 87b1, 87b2, 87c1, and 87c2 are formed on both sides of the bore 87a. The projection units 71a and 71c are inserted into the bores 87b1 and 87b2, and the projection units 71b and 71d are inserted into the bores 87c1 and 87c2.

The tip of the hard tip portion 87 is covered by a rubber tip cap 89, and the circumference of the hard tip portion 87 is covered by an outer sheath tube (not shown). Bores 89a, 89b, 89c, . . . corresponding to the bores 87a, 87b1, 87b2, 87c1, 87c2, . . . of the hard tip portion 87 are formed in the rubber tip cap 89 to open the observation window 40 by the objective lens unit 39 or the irradiation openings 37a and 37b of the projection units 71a to 71d.

Figure 7:
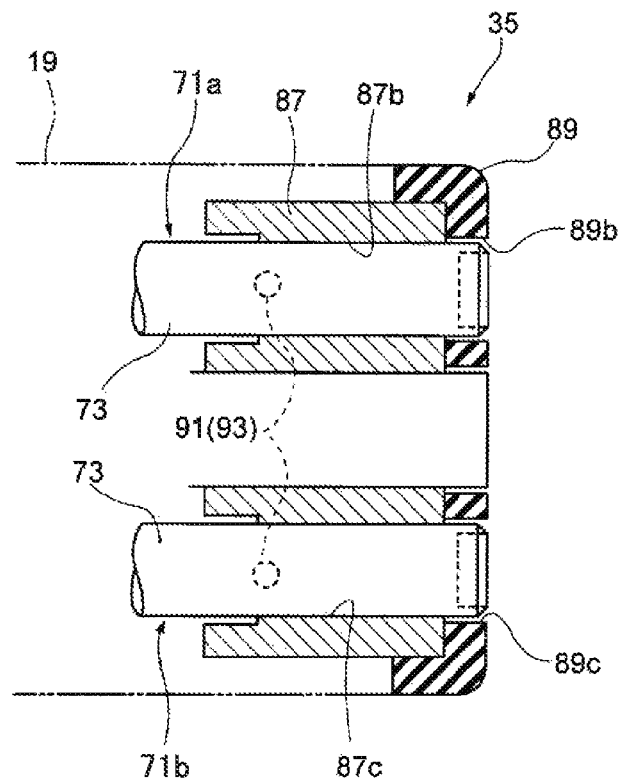
FIG. 7 is a sectional view taken along the line A-A of FIG. 5.

FIG. 7 is a sectional view taken along the line A-A of FIG. 5. The projection units 71a and 71b are inserted into the bores 87b1 and 87c1 of the hard tip portion 87 and then fastened with set screws 93 from a pair of horizontal holes 91 (see FIGS. 5 and 6) communicating with the bores 87b1 and 87c1, such that the projection units 71a and 71b are fixed to the hard tip portion 87. Similarly, the projection units 71c and 71d are fastened with set screws 93 and fixed to the hard tip portion 87.

According to the configuration of the endoscope including the projection units 71a to 71d, the projection units 71a to 71d are detachably fixed by the set screws 93 in a state of being inserted into the bores 87b1, 87b2, 87c1, and 87c2 of the hard tip portion 87. For this reason, the replacement of the projection units 71a to 71d is easily done, thereby improving the maintenance of the endoscope. That is, when attenuation of illumination light intensity or changes in color occur due to the long-term use of the endoscope, replacement with a new projection unit is simply done.

Next, illumination patterns through which laser light from the laser light sources LD1 to LD5 are suitably combined and emitted by the projection units 71a to 71d to generate various kinds of illumination light will be described.

Figure 8:
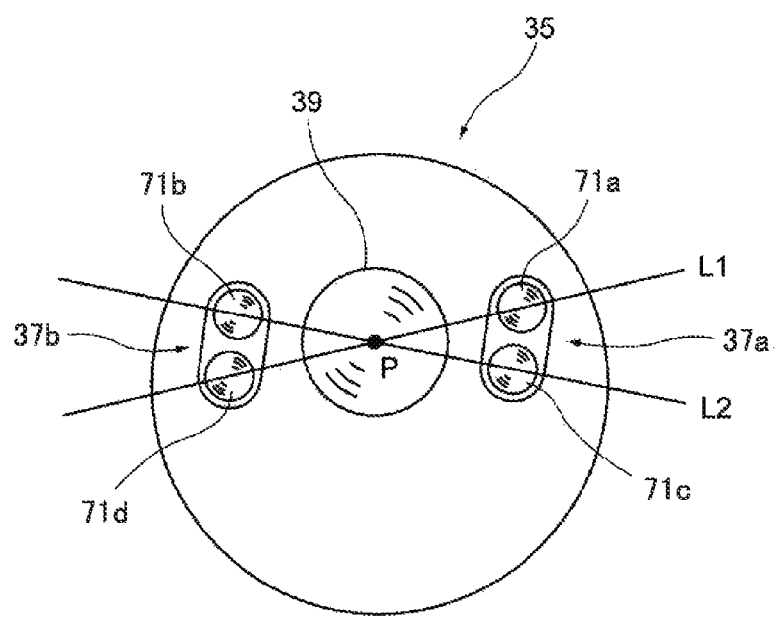
FIG. 8 is a front view of the tip portion of the endoscope shown in FIG. 5 when viewed from a B direction.

FIG. 8 is a front view of the tip portion of the endoscope 11 shown in FIG. 5 when viewed from a B direction. As described above, the projection units 71a to 71d are arranged on both sides of the objective lens unit 39 such that the projection units 71a and 71c perform irradiation from the irradiation opening 37a, and the projection units 71b and 71d perform irradiation from the irradiation opening 37b. A pair of projection units 71a and 71d including the fluorescent substances (see FIG. 3A) are arranged such that a line L1 connecting the positions of the protective glasses 75 (see FIGS. 3A and 3B) serving as an illumination window cuts across the region of the objective lens unit 39 serving as the observation window 40. A pair of projection units 71b and 71c including the optical deflection/diffusion members 58

(see FIG. 3B) are arranged such that a line L2 connecting the positions of the protective glasses 75 (see FIGS. 3A and 3B) cuts across the region of the objective lens unit 39.

The projection units 71a to 71d are arranged in the increased space efficiency such that the lines L1 and L2 have a cross point P in the region of the objective lens unit 39. That is, the projection units 71a and 71d which irradiate white illumination light are arranged at the positions with the objective lens unit 39 of the tip portion 35 sandwiched therebetween, and irradiate white light from both sides of the objective lens unit 39, thereby preventing the occurrence of illumination irregularity.

Although in the example of the drawing, a four-light type is provided in which the four projection units 71a to 71d, including the two projection units 71a and 71b with the fluorescent substances 57, are arranged in the tip portion 35 of the endoscope 11 at the positions with the objective lens unit 39 for the image pickup device 21, the invention is not limited thereto. If one projection unit includes the fluorescent substance 57, a two-light type may be provided in which the two projection units 71a and 71c or 71b and 71d, preferably, the two projection units 71a and 71d or 71b and 71c are arranged in the tip portion 35 of the endoscope 11 at the positions with the objective lens unit 39 for the image pickup device 21 sandwiched therebetween.

Next, the processor 13 will be described in detail with reference to FIG. 2.

As shown in FIG. 2, the processor 13 has a digital signal processing section (DSP (Digital Signal Processor)) 64 which performs a digital signal process on the digital image signal of each observation mode transmitted from the endoscope 11, an image processing section 63 which performs an image process according to each observation mode on image data subjected to the digital signal process of each observation mode, a control section 65 which performs display control for displaying an observation image based on image data subjected to image process on the display section 15 or controls the respective sections of the endoscope 11, the light source device 12, and the processor 13, and a storage section 67 which stores the image data signal of the captured image of each observation mode.

The DSP 64 receives the digital image signal of the captured image of each observation mode captured by the image pickup device 21 and transmitted from the AFE 61 of the imaging system of the endoscope 11 through the connector portion 25b, and performs various processes, such as color separation, color interpolation, color correction, white balance adjustment, gamma correction, and contour enhancement, on the received digital image signal to generate captured image data of each observation mode subjected to the digital signal process. Image data of the captured image of each observation mode generated by the DSP 64 is transmitted to the image processing section 63 and, if necessary, is stored in the storage section 67.

As shown in FIG. 2, the image processing section 63 performs an image process according to each observation mode on image data of the captured data of each observation mode subjected to the digital signal process in the DSP 64. The image processing section 63 has a normal light image processing section 102 which performs an image process on the captured image using broadband light (white light) in the normal observation mode, and a special light image processing section 104 which performs an image process on the captured image using broadband light and narrowband light in the special light observation mode. Image data of the captured image of each observation mode subjected to the image process in the image processing section 63 is transmitted to the control section 65 and, if necessary, is stored in the storage section 67.

In the normal observation mode, the normal light image processing section 102 performs a predetermined image process suitable for a normal observation image by white light from the narrowband light source 41a of the normal light source section 41 of the light source device 12 and the fluorescent substance 57 on image data (RGB image data of white light) of the captured image using white light transmitted from the DSP 64 or read from the storage section 67, outputs normal light image data, stores normal light image data in the storage section 67, and causes the display section 15 to display a normal observation image by white light.

In the special light observation mode using narrowband light, the special light image processing section 104 performs a predetermined image process suitable for a special light observation image by narrowband light on image data of the captured image transmitted from the DSP 64 or read from the storage section 67, and outputs special light image data. That is, an image process is performed on the captured image using white light from the normal light source section 41 and narrowband light N2 and N3 from the narrowband light sources 43a and 43b of the narrowband light source section 43.

In the embodiment of the drawing, the special light image processing section 104 performs an image process for calculating oxygen saturation, blood vessel depth, blood volume, and the like as the biological function information of the region to be observed of the subject to generate an oxygen saturation image. The special light image processing section 104 generates the oxygen saturation image or information regarding the blood vessel depth, blood volume, and the like.

Hereinafter, the control of the light source device 12 in the special light observation mode and the special light image processing section of the image processing section of the processor in the endoscope apparatus of the invention will be described.

Figure 9:
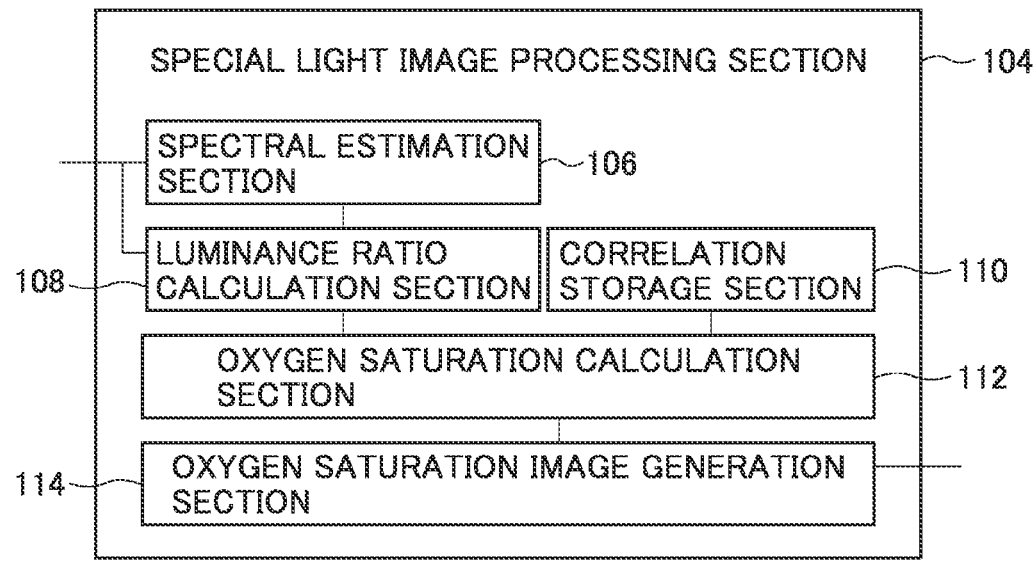
FIG. 9 is a block diagram showing the configuration of an example of a special light image processing section of an image processing section in the endoscope apparatus shown in FIG. 2.
Figure 10:
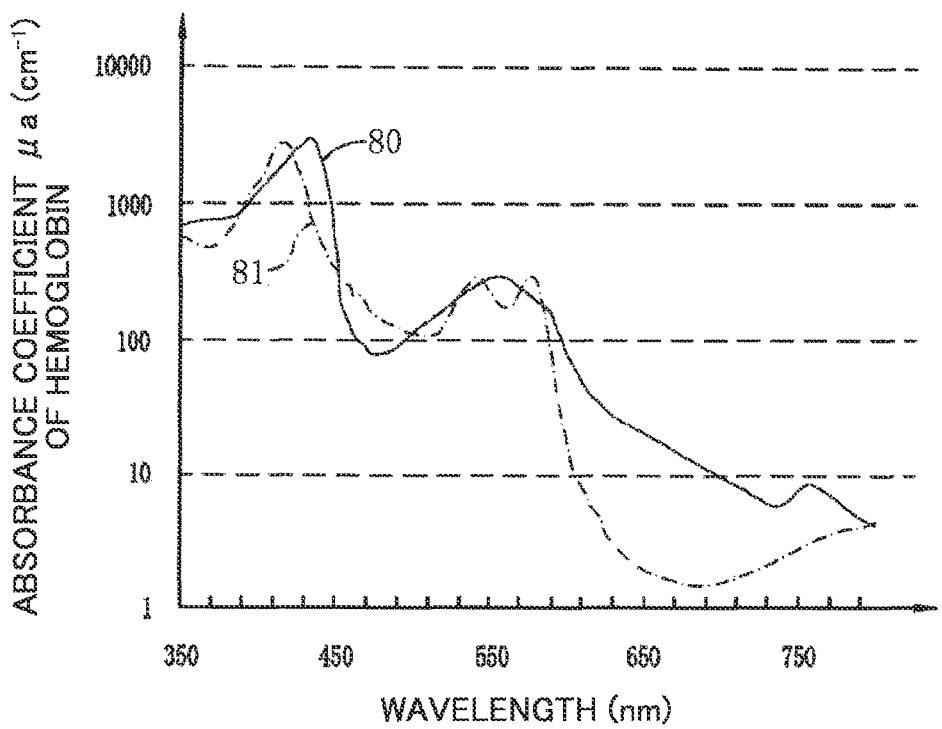
FIG. 10 is a graph showing the wavelength dependency of an absorption coefficient of hemoglobin in a blood vessel.
Figure 11:
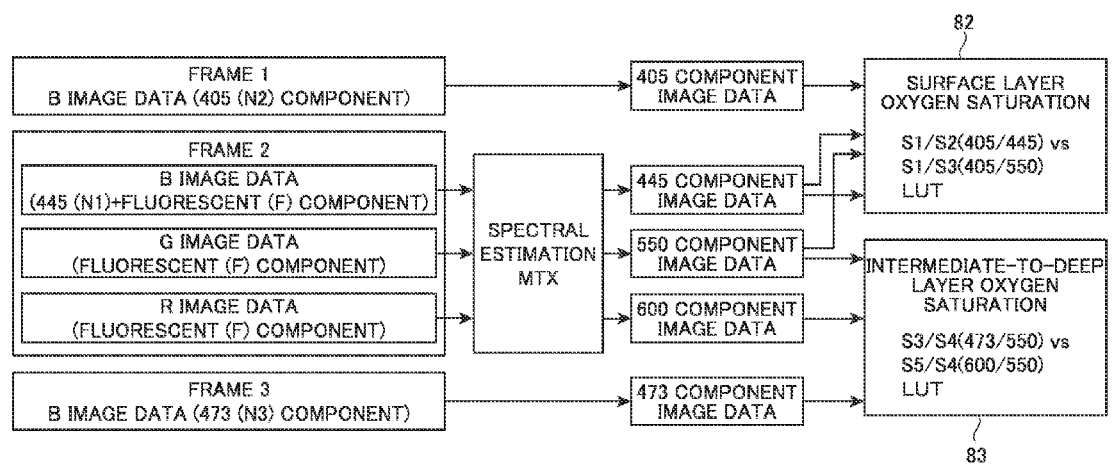
FIG. 11 is an explanatory view illustrating a process for calculating oxygen saturation in a special light mode of the endoscope apparatus shown in FIG. 1.
Figure 12:
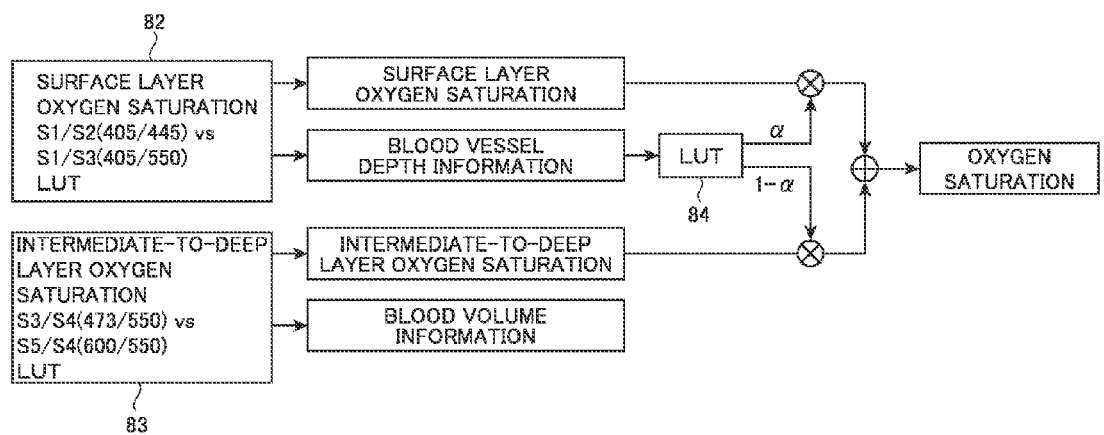
FIG. 12 is an explanatory view illustrating a process for calculating oxygen saturation in a special light mode of the endoscope apparatus shown in FIG. 1.
Figure 13:
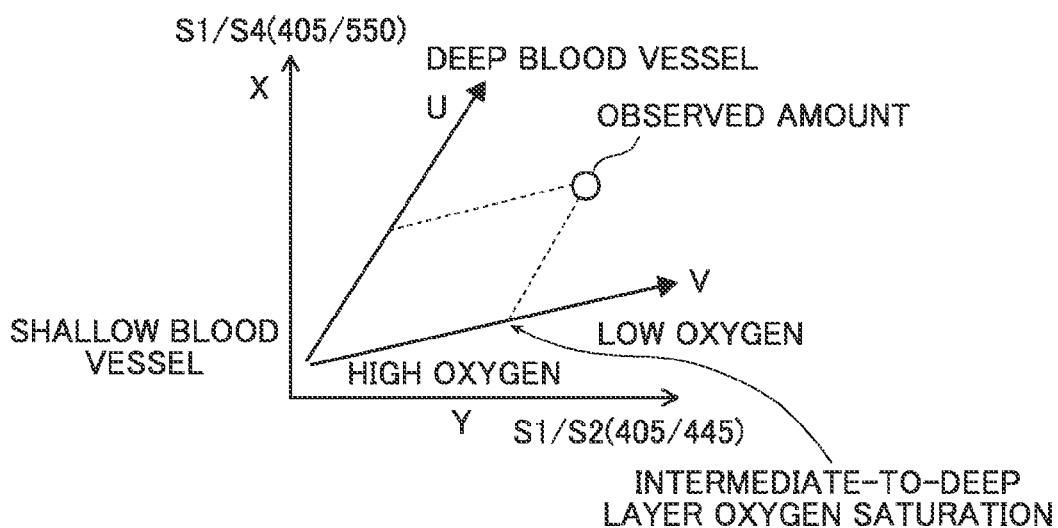
FIG. 13 is a graph showing the correlation between the spectral luminance ratio of pixels of a captured image, a blood vessel depth, and oxygen saturation.
Figure 14:
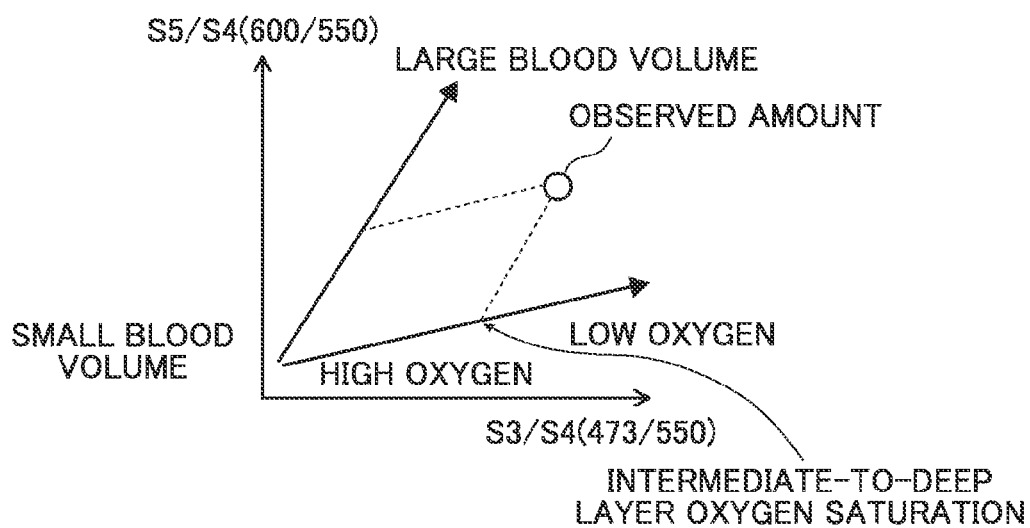
FIG. 14 is a graph showing the correlation between the spectral luminance ratio of pixels of a captured image, blood volume, and oxygen saturation.

FIG. 9 is a block diagram showing the configuration of an example of the special light image processing section of the image processing section shown in FIG. 2. FIG. 10 is a graph showing the wavelength dependency of the absorption coefficient of hemoglobin in a blood vessel. FIGS. 11 and 12 are explanatory views illustrating a process (visualization algorithm) for calculating oxygen saturation in the special light mode. FIG. 13 is a graph showing the correlation between the spectral luminance ratio (S1/S3, S1/S2) of pixels of a captured image, blood vessel depth, and oxygen saturation. FIG. 14 is a graph showing the correlation between the spectral luminance ratio (S5/S4, S3/S4) of pixels of a captured image, blood volume, and oxygen saturation.

As shown in FIG. 9, the special light image processing section 104 has a spectral estimation section 106, a luminance ratio calculation section 108, a correlation storage section 110, an oxygen saturation calculation section 112, and an oxygen saturation image generation section 114. In the special light mode, the special light image processing section 104 calculates information regarding the oxygen saturation of hemoglobin in the blood of the subject using the wavelength dependency of the absorption coefficient of hemoglobin in the blood shown in FIG. 10 on the basis of captured image data by pseudo white light from the narrowband light source 41a of the normal light source section 41 and the fluorescent substance 57 and narrowband light N2 and N3 from the narrowband light sources 43a and 43b of the narrowband light source section 43, and outputs an oxygen saturation image for visualizing the oxygen saturation on the basis of information regarding the calculated oxygen saturation, for example, for pseudo-color displaying the distribution of oxygen saturation.

In the special light mode, as shown in FIG. 11 and Table 1, the narrowband light source 41a of the normal light source section 41 and the narrowband light sources 43a and 43b of the narrowband light source section 43 are used, and in the first frame, B image data (hereinafter, referred to as 405 component image data) of a spectrum of only the narrowband light N2 (405 nm) component from the narrowband light source 43a (LD405) is acquired. In the second frame, captured image data (RGB image data of white light) obtained with pseudo white light resulting from the combination of the narrowband light source 41a (LD445) and the fluorescent substance 57 is acquired. In the third frame, 473 component image data which is B image data of a spectrum of only the component narrowband light N3 (473 nm) from the narrowband light source 43b (LD445) is acquired.

TABLE 1

|  | Frame 1 | Frame 2 | Frame 3 |
| --- | --- | --- | --- |
| Light Source | LD405 | LD445 + Fluorescent Substance | LD473 |

RGB image data of white light obtained in the frame 2 is obtained by the image pickup device 21 having the color filters shown in FIG. 5B from reflected light when white light (BW) shown in FIG. 5A is irradiated onto the biological object. Thus, B image data obtained in the frame 2 is B image data constituted by the narrowband light N1 (445 nm) component from the narrowband light source 41a (LD445) shown in FIG. 5A and the fluorescence (F) component generated upon excitation by narrowband light N1. G image data obtained in the frame 2 is G image data constituted by the fluorescence (F) component shown in FIG. 5A, and R image data obtained in the frame 2 is R image data constituted by the fluorescence (F) component shown in FIG. 5A.

These pieces of RGB image data are the same as image data (RGB image data of white light) of the captured image by white light obtained in the normal light mode. As in the normal light mode, in the normal light image processing section 102, a predetermined image process suitable for a normal observation image is performed on RGB image data, such that RGB image data is output as normal observation image data and stored in the storage section 67.

In the special light mode, the light source control section 49 performs turn-on control such that the narrowband light sources 41a, 43a, and 43b are turned on only in the first, second, and third frames. The imaging control section 62 drives the image pickup device 21 in each frame and performs imaging frame control so as to acquire the respective pieces of image data.

That is, in the first frame, only narrowband light N2 of 405 nm shown in FIG. 4A is irradiated onto the subject. For this reason, 405 component image data is acquired by the image pickup device 21 having the color filters shown in FIG. 4B and stored in the storage section 67.

Next, in the second frame, white light BW shown in FIG. 4A is irradiated onto the subject. For this reason, RGB image data of white light BW is acquired by the image pickup device 21 having the color filters shown in FIG. 4B and stored in the storage section 67.

In the third frame, only narrowband light N3 of 473 nm shown in FIG. 4A is irradiated onto the subject. For this reason, 473 component image data is acquired by the image pickup device 21 having the color filters shown in FIG. 4B and stored in the storage section 67.

The spectral estimation section 106 reads RGB image data of white light BW acquired in the second frame from the storage section 67, and obtains 445 component image data of the B region, 550 component image data of the G region, and 600 component image data of the R region from read RGB image data by spectral estimation. That is, as shown in FIG. 11, the spectral estimation section 106 performs spectral estimation using matrix computation (MTX) to obtain 445 component image data, 550 component image data, and 600 component image data from RGB image data of white light acquired in the second frame.

The spectral estimation method which obtains three pieces of 445 component image data, 550 component image data, and 600 component image data from RGB image data is not particularly limited, and a known spectral estimation method in the related art may be used. For example, a spectral estimation method described in JP 2003-93336 A may be used.

As shown in FIG. 11, the luminance ratio calculation section 108 calculates two kinds of luminance ratios of pixels of two pieces of spectral image data within three pieces of spectral image data for computing the blood vessel depth and the surface layer oxygen saturation from 405 component image data and 473 component image data 445 obtained in the first and third frames and component image data, 550 component image data, and 600 component image data obtained by spectral estimation of the spectral estimation section 106 in the second frame. The luminance ratio calculation section 108 also calculates two kinds of luminance ratios of pixels of two pieces of spectral image data within three pieces of spectral image data for computing the blood volume and the intermediate-to-deep layer oxygen saturation.

First, in order to compute the blood vessel depth and the surface layer oxygen saturation, the luminance ratio calculation section 108 reads, from the storage section 67, 405 component image data acquired in the first frame and 445 component image data and 550 component image data obtained by spectral estimation of the spectral estimation section 106 in the second frame, and specifies the blood vessel of a biological mucosa, preferably, a blood vessel region including the surface layer blood vessel from read 405 component image data, 445 component image data, and 550 component image data. As the method of specifying a blood vessel, for example, a method may be used in which a blood vessel region is obtained from a difference between the luminance value of the blood vessel portion and the luminance value of another portion.

As shown in FIG. 11, when the luminance value of the pixel of 405 component image data corresponding to reflected light of one kind of narrowband light in a wavelength range such that, with regard to the pixels at the same position in the specified blood vessel region, the absorbance coefficients (see FIG. 10) of reduced hemoglobin and oxidized hemoglobin become equal in accordance with the oxygen saturation of hemoglobin in the blood is S1, and the luminance values of pixels of 445 component image data and 550 component image data corresponding to reflected light of two kinds of narrowband light in a wavelength range in which the magnitude relationship of the absorbance coefficients is reversed are respectively S2 and S4, the luminance ratio calculation section 108 obtains first and second luminance ratios S1/S2 and S1/S4.

Next, in order to compute the blood volume and the intermediate-to-deep layer oxygen saturation, the luminance ratio calculation section 108 reads, from the storage section 67, 550 component image data and 600 component image data obtained by spectral estimation of the spectral estimation section 106 in the second frame and 473 component image data acquired in the third frame, and specifies a blood vessel region including the blood vessel of a biological mucosa, preferably, a blood vessel region of the intermediate-to-deep layer blood vessel from read 405 component image data, 445 component image data, and 550 component image data. The blood vessel region which is specified so as to compute the blood vessel depth and the surface layer oxygen saturation may be used as it is without specifying the blood vessel region.

As shown in FIG. 11, when the luminance values of pixels of 473 component image data and 600 component image data corresponding to reflected light of two kinds of illumination light in a wavelength range in which, with regard to the pixels at the same position in the specified blood vessel region, the magnitude relationship between the absorbance coefficients (see FIG. 10) of reduced hemoglobin and oxidized hemoglobin is reversed in accordance with the oxygen saturation of hemoglobin in the blood are S3 and S5, and the luminance value of the pixel of 550 image data corresponding to reflected light of one illumination light in a wavelength range in which the absorbance coefficients become equal is S4, the luminance ratio calculation section 108 obtains third and fourth luminance radios S3/S4 and S5/S4.

The correlation storage section 110 stores a first correlation between the first and second luminance ratios S1/S2 and S1/S4, the blood vessel depth, and the surface layer oxygen saturation, for example, the correlation shown in FIG. 13, and a second correlation between the first and second luminance ratios S3/S4 and S5/S4, the blood volume, and the intermediate-to-deep layer oxygen saturation, for example, the correlation shown in FIG. 14. The first and second correlations are correlations when the blood vessel has the absorbance coefficient of hemoglobin shown in FIG. 10, and are obtained by analyzing multiple image data accumulated by previous diagnosis or the like.

As shown in FIG. 10, hemoglobin in the blood has an absorbance characteristic such that an absorbance coefficient μa changes depending on the wavelength of light to be irradiated. The absorbance coefficient μa indicates an absorbance which is the magnitude of light absorption of hemoglobin. For example, the absorbance coefficient μa is a coefficient of Expression I0 exp(−μaxx) which represents the attenuation situation of light irradiated onto hemoglobin. I0 is the intensity of light irradiated onto the subject tissue from the light source device, and x (cm) is the depth to the blood vessel in the subject tissue.

As shown in FIG. 10, reduced hemoglobin 80 which is not bound to oxygen and oxidized hemoglobin 81 which is bound to oxygen have different absorbance characteristics, and there is a difference in the absorbance excluding an isosbestic point (in FIG. 10, a cross point of hemoglobin 80 and 81) representing the same absorbance (absorbance coefficient μa). there is a difference in the absorbance, even when light having the same intensity and wavelength is irradiated onto the same blood vessel, the luminance value changes. Even when light having the same intensity is irradiated, if light is different in wavelength, the absorbance coefficient μa changes, causing a change in the luminance value.

In general, since the distribution of FIG. 10 changes nonlinearly depending on an imaging-target site, it is necessary to obtain the distribution in advance by actual biological tissue measurement, light propagation simulation, or the like.

As shown in FIG. 13, the correlation storage section 110 associates the coordinates of a luminance coordinate system representing the first and second luminance ratios S1/S2 and S1/S4 with the coordinates of a blood vessel information coordinate system representing the surface layer oxygen saturation and the blood vessel depth, thereby storing the first correlation. The luminance coordinate system is the XY coordinate system in which the X axis represents the first luminance ratio S1/S2 and the Y axis represents the second luminance ratio S1/S4. The blood vessel information coordinate system is the UV coordinate system which is provided on the luminance coordinate system and in which the U axis represents the blood vessel depth and the V axis represents the oxygen saturation. The U axis has a positive slope because the blood vessel depth has a positive correlation with the luminance coordinate system. As the position on the U axis moves diagonally upward right, the depth of the blood vessel increases; as the position on the U axis moves diagonally downward left, the depth of the blood vessel decreases. The V axis has a positive slope since the oxygen saturation also has a positive correlation with the luminance coordinate system. As the position on the V axis moves diagonally upward right, the oxygen saturation decreases; as the position on the V axis moves diagonally downward left, the oxygen saturation is low increases.

It is preferable that the first correlation shown in FIG. 13 is stored in the correlation storage section 110 as a surface layer oxygen saturation (S1/S2 (405/445) vs S1/S4 (405/550)) lookup table (LUT) 82, as shown in FIGS. 11 and 12.

As shown in FIG. 14, the correlation storage section 110 associates the coordinates of a luminance coordinate system representing third and fourth luminance ratios S3/S4 and S5/S4 with the coordinates of a blood vessel information coordinate system representing the oxygen saturation and the blood volume, thereby storing the second correlation. The luminance coordinate system is an XY coordinate system in which the X axis represents the third luminance ratio S3/S4 and the Y axis represents the fourth luminance ratio S5/S4. The blood vessel information coordinate system is the UV coordinate system which is provided on the luminance coordinate system and in which the U axis represents the blood volume and the V axis represents the oxygen saturation. The U axis has a positive slope because the blood volume has a positive correlation with the luminance coordinate system. As the position on the U axis moves diagonally upward right, the blood volume increases; as the position on the V axis moves diagonally downward left, the blood volume decreases. The V axis has a positive slope because the oxygen saturation also has a positive correlation with the luminance coordinate system. As the position on the V axis moves diagonally upward right, the oxygen saturation decreases; as the position on the V axis moves diagonally downward left, the oxygen saturation increases.

It is preferable that the second correlation shown in FIG. 14 is stored in the correlation storage section 110 as an intermediate-to-deep layer oxygen saturation (S3/S4 (473/550) vs S5/S4 (600/550)) lookup table (LUT) 83, as shown in FIGS. 11 and 12.

The calculation of the blood vessel depth and the oxygen saturation using the luminance values S1, S2, and S4, and the calculation of the blood volume and the oxygen saturation using the luminance values S3, S4, and S5 will be described.

In general, if light enters the mucosal tissue of the subject, a part of light is absorbed in the blood vessel, and another part of light having not been absorbed returns as reflected light. At this time, the deeper the blood vessel is, the larger the influence of scattering from overlying tissue becomes.

On the other hand, light in a wavelength range of 400 to 560 nm has features that the invasion depth into the mucosa is comparatively small, the scattering coefficient in the mucosal tissue is large, and the wavelength dependency significantly changes. For this reason, with the use of light in this wavelength range as illumination light, it is possible to obtain blood information including information regarding the depth of the blood vessel and the oxygen saturation.

Light in a wavelength range of 470 to 700 nm has features that the invasion depth into the mucosa is comparatively large, the scattering coefficient in the mucosal tissue is small, and the wavelength dependency is small. For this reason, with the use of light in this wavelength range as illumination light, it is possible to obtain blood information including information regarding the blood volume and the oxygen saturation without reducing an influence of the depth of the blood vessel.

Therefore, according to the invention, in the wavelength ranges 400 to 560 nm, 460 to 700 nm, and 400 to 560 nm including reflected light in two or more wavelength ranges in which the absorbance coefficient changes depending on the oxygen saturation of hemoglobin in the blood and reflected light in one or more wavelength ranges in which there is no change in the absorbance coefficient, image signals corresponding to three or more different reflected light are used to calculate the oxygen saturation of hemoglobin in the blood.

That is, taking into consideration the absorbance characteristic of hemoglobin shown in FIG. 10, the wavelengths at which there is a difference in the absorbance due to the oxygen saturation are 445 nm and 405 nm, and a short-wavelength region having a short invasion depth is necessary so as to extract blood vessel depth information. For this reason, it is preferable that spectral image data of three kinds of wavelength components includes at least one piece of spectral image data having a wavelength region in which the center wavelength is equal to or smaller than 450 nm. In this embodiment, such spectral image data narrowband light corresponds to 405 component image data and 445 component image data. Even when the oxygen saturation is the same, if the wavelength is different, the value of the absorption coefficient differs, and the invasion depth into the mucosa differs. Therefore, with the use of the characteristic of light whose invasion depth differs depending on the wavelength, it is possible to obtain the correlation between the luminance ratio and the blood vessel depth shown in FIG. 13.

The following three features can be thought from the wavelength dependency of the absorbance coefficient of hemoglobin in the blood shown in FIG. 10.

The absorbance coefficient significantly changes depending on changes in the oxygen saturation in the vicinity of the wavelength 470 nm (for example, a B wavelength range of the center wavelength 470 nm±10 nm), and the absorbance coefficient of oxidized hemoglobin 81 is larger than the absorbance coefficient of reduced hemoglobin 80.

There is little influence of the oxygen saturation in the vicinity of 550 nm (for example, a G wavelength range of the center wavelength 550 nm±10 nm). That is, a difference between the absorbance coefficient of oxidized hemoglobin 81 and the absorbance coefficient of reduced hemoglobin 80 is regarded to be small.

The absorbance coefficient seems to apparently change significantly in the vicinity of 600 nm (for example, an R wavelength range of the center wavelength 600 nm±10 nm) depending on the oxygen saturation, and the absorbance coefficient of reduced hemoglobin 80 is larger than the absorbance coefficient of oxidized hemoglobin 81. However, since the value of the absorbance coefficient is extremely small in this range, as a result, it can be thought that there is little influence of the oxygen saturation.

There are the following two features from the reflection spectrum of the mucosa.

Although it seems that there is little influence of hemoglobin in the vicinity of the wavelength 600 nm, since absorption occurs in the vicinity of the wavelength 550, the larger the blood volume (corresponding to the size of the blood vessel or the density of the blood vessel), the larger the difference between reflectance in the vicinity of the wavelength 550 (G wavelength range) and reflectance in the vicinity of the wavelength 600 nm (R wavelength range).

The lower the oxygen saturation, or the larger the blood volume, the larger the difference between reflectance in the vicinity of the wavelength 470 nm (B wavelength range) and reflectance in the vicinity of the wavelength 550 nm (G wavelength range).

For this reason, the third luminance ratio S3/S4 between the luminance value of the pixel of 473 component image data and the luminance value of the pixel of 550 component image data changes depending on both the oxygen saturation and the blood volume. The fourth luminance ratio S5/S4 between the luminance value of the pixel of 600 component image data and the luminance value of the pixel of 550 component image data changes mainly depending on the blood volume. Therefore, with the use of this feature, it is possible to separate the oxygen saturation and the blood volume from spectral images of three wavelength ranges including wavelength ranges in the vicinity of the wavelength 470 nm, the wavelength 550 nm, and the wavelength 600 nm, and to accurately calculate the respective values.

Therefore, if a graph is created on the basis of this feature, it is possible to obtain a graph representing the correlation between the third and fourth luminance ratios S3/S4 and S5/S4, the blood volume, and the oxygen saturation shown in FIG. 14.

As shown in FIG. 12, the oxygen saturation calculation section 112 specifies the oxygen saturation and the blood vessel depth corresponding to the first and second luminance ratios S1/S2 and S1/S4 calculated by the luminance ratio calculation section 108 on the basis of the surface layer oxygen saturation LUT 82 representing the first correlation stored in the correlation storage section 110. That is, the oxygen saturation and the blood vessel depth information are calculated from the first and second luminance ratios S1/S2 and S1/S4 using the surface layer oxygen saturation LUT 82. The oxygen saturation calculation section 112 specifies corresponding coordinates (X,Y) in the luminance coordinate system shown in FIG. 13 from the first and second luminance ratios S1/S2 and S1/S4 for a predetermined pixel in the blood vessel region calculated by the luminance ratio calculation section 108, obtains the value on the UV coordinate system with the specified coordinates (X,Y) as coordinates on the blood vessel information coordinate system, and specifies coordinates (U,V). Therefore, it is possible to obtain the blood vessel depth information U and the oxygen saturation V for a pixel at a predetermined position in the blood vessel region.

Similarly, the oxygen saturation calculation section 112 calculates the blood volume information and the oxygen saturation corresponding to the third and fourth luminance ratios S3/S4 and S5/S4 calculated by the luminance ratio calculation section 108 on the basis of the intermediate-to-deep layer oxygen saturation LUT 83 representing the second correlation stored in the correlation storage section 110. That is, the oxygen saturation and the blood volume information are calculated from the third and fourth luminance ratios S3/S4 and S5/S4 using the intermediate-to-deep layer oxygen saturation LUT 83.

In the oxygen saturation calculation section 112, as shown in FIG. 12, in order to calculate the oxygen saturation according to the blood vessel depth from the thus-obtained blood vessel depth information using the LUT 84, weighting coefficients α and 1-α for weighting the calculated surface layer oxygen saturation and the intermediate-to-deep layer oxygen saturation are calculated.

The thus calculated weighting coefficient α and the surface layer oxygen saturation are multiplied, the weighting coefficient 1-α and the surface layer oxygen saturation are multiplied, and the multiplication results are added to calculate the weighted oxygen saturation in accordance with the blood vessel depth.

In this way, it is possible to calculate the oxygen saturation suitable for the blood vessel depth.

The oxygen saturation image generation section 114 includes a color table (not shown) in which color information is allocated in accordance with the magnitude of the oxygen saturation. In the color table, colors are allocated to be clearly distinguishable in accordance with the degree of oxygen saturation, for example, cyan at the time of low oxygen saturation, magenta at the time of middle oxygen saturation, and yellow at the time of high oxygen saturation. The oxygen saturation image generation section 114 specifies color information corresponding to the oxygen saturation calculated by the oxygen saturation calculation section 112 using the color table.

The color table is switchable in accordance with an instruction input from the input section 17, and is selected in accordance with an observation site, such as stomach, duodenum, or small intestine.

If the color information is specified for all pixels in the blood vessel region, the oxygen saturation image generation section 114 reads normal light image data of the normal observation image obtained with white light which is generated in the normal light image processing section 102 in the first frame and stored in the storage section 67, and reflects and superimposes the color information in and on read normal light image data, that is, synthesizes the color information with the normal observation image to generate oxygen saturation image data in which the oxygen saturation of hemoglobin in the blood is reflected (pseudo-color display).

Oxygen saturation image data generated special light image processing section 104, the blood vessel depth information, and the blood volume information are transmitted to the control section 65, and become an oxygen saturation image including the blood vessel depth information and/or the blood volume information for endoscope observation together with various kinds of information in the control section 65. Then, the oxygen saturation image is displayed on the display section 15 as a detailed diagnostic image, and the oxygen saturation, particularly, the oxygen saturation suitably calculated in accordance with the blood vessel depth is visualized with high precision. If necessary, the oxygen saturation image including the blood vessel depth information and/or the blood volume information is stored in the storage section 67 constituted by a memory or a storage device.

As described above, during the special light mode, in the frame 1, 405 component image data by narrowband light N2 having the wavelength 405 nm is acquired. In the frame 2, 445 component image data, 550 component image data, and 600 component image data are acquired by spectral estimation from RGB image data obtained with narrowband light N1 having the wavelength of 445 nm and the fluorescent substance 57. In the frame 3, 473 component image data obtained with narrowband light N3 having the wavelength of 473 nm is acquired. For this reason, it is possible to use adjacent frames 1 and 2 for the calculation of the surface layer oxygen saturation and the blood vessel depth, and to use adjacent frames 2 and 3 for the calculation of the intermediate-to-deep layer oxygen saturation and the blood volume. Therefore, for the calculation of the surface layer oxygen saturation and the blood vessel depth, and for the calculation of the intermediate-to-deep layer oxygen saturation and the blood volume, it is possible to reduce the influence of misalignment when the subject moves, and to compute the oxygen saturation or the blood vessel depth and the blood volume accurately and with high precision, thereby displaying and visualizing accurate and high-precision oxygen saturation on the display section 15. The oxygen saturation image including the visualized biological function information is a high-precision and accurate oxygen saturation image including the blood vessel depth information or the blood volume information, and is an image suitable for detailed diagnosis capable of diagnosing a lesion site or the like in detail and accurately.

According to the invention, a blood vessel depth image generation section may be provided to generate the blood vessel depth information as a blood vessel depth image in which color information is allocated in accordance with the degree of the blood vessel depth. The blood vessel depth image generation section includes a color table in which color information is allocated in accordance with the degree of the blood vessel depth. In the color table, colors are allocated to be clearly distinguishable in accordance with the degree of the blood vessel depth, for example, blue when the blood vessel depth is the surface layer, green when the intermediate layer, and red when the deep layer. The blood vessel depth image generation section specifies the color information corresponding to the blood vessel depth information U calculated by the oxygen saturation calculation section 112 from the color table.

If the color information is specified for all pixels in the blood vessel region, similarly to the oxygen saturation image generation section 114, the blood vessel depth image generation section reads normal light image data of the normal observation image stored in the storage section 67, and reflects and superimposes the color information in and on read normal light image data, that is, synthesizes the color information image with the normal observation image to generate blood vessel depth image data in which the blood vessel depth information is reflected. The generated blood vessel depth image data is stored in the storage section 67 again. The color information may be reflected in each piece of spectral image data of each wavelength component or a synthesized image of spectral image data, instead of normal light image data.

The control section 65 has a display control section 65*a* which causes the observation image based on image data subjected to the image process to be displayed on the display section 15 in each diagnosis mode, and a controller 65*b* which controls the respective sections of the endoscope 11, the light source device 12, and the processor 13.

The display control circuit 65*a* is used to read one image or a plurality of images from the storage section 67 and to display the read image on the display section 15. As an image display form, various patterns are considered. For example, a normal image may be displayed on one side of the display section 15, and the oxygen saturation image may be displayed on another side. A blood vessel depth image representing the blood vessel depth information or a blood volume image representing the blood volume information may be displayed.

Of the oxygen saturation image, the blood vessel depth image, and the image representing the blood volume, one of the blood vessel depth image, the oxygen saturation image, and the blood vessel depth image selected by an image selector SW (not shown) of the input section 17, or two or more images may be displayed. In the oxygen saturation image, for example, the blood vessel image representing low oxygen saturation can be displayed cyan, the blood vessel image representing middle oxygen saturation can be displayed magenta, and the blood vessel image representing high oxygen saturation can be displayed yellow. In the blood vessel depth image, for example, the blood vessel image representing the surface layer blood vessel can be displayed blue, the blood vessel image representing the intermediate layer blood vessel can be displayed green, and the blood vessel image representing the deep layer blood vessel can be displayed red.

The oxygen saturation, the blood vessel depth, the blood volume, and the like may be displayed on the display section 15 as linear images, such as character information.

As shown in Table 1, the controller 65b transmits a turn-on control signal of each light source to the light source control section 49 such that, in the special light mode, the light source control section 49 of the light source device 12 performs turn-on control of the narrowband light source 41a of the normal light source section 41 and the narrowband light sources 43a and 43b of the narrowband light source section 43 in a predetermined order in each imaging frame, thereby controlling the light source control section 49. The controller 65b transmits an imaging instruction signal to the imaging control section 62 such that the imaging control section 62 of the endoscope 11 allows imaging by the image pickup device 21 in accordance with the turn-on of each light source by the light source control section 49 in each imaging frame, thereby controlling the imaging control section 62.

The storage section 67 is constituted by a memory or a storage device, and stores image data of the captured image of each observation mode, image data of the oxygen saturation image generated by the image processing section 63, the blood vessel depth image, and the image representing the blood volume, and various kinds of data or programs necessary for driving, operation, control, and the like of the endoscope apparatus 10, particularly, the endoscope 11, the processor 13, the light source device 12, and the like.

Next, the function of an endoscope diagnosis apparatus of this embodiment will be described.

First, the function in the normal observation mode will be described.

An instruction of the observation mode or the like is input from the input section 17 of the endoscope apparatus 10 to the control section 65 of the processor 13, and the observation mode is set to the normal observation mode.

In the normal observation mode, the operation of the light source control section 49 of the light source device 12 is controlled by the control section 65 of the processor 13. Then, the narrowband light source 41a (LD445) of the normal light source section 41 is turned on, and the narrowband light sources 43a and 43b of the narrowband light source section 43 are turned off. Thus, excitation light E (narrowband light N1) for normal observation is emitted from LD445.

In the endoscope 11, excitation light E for normal observation emitted from the light source device 12 is guided to the fluorescent substances 57 of the scope tip portion 35 by the optical fibers 55a and 55d. Thus, pseudo white light is emitted from the fluorescent substance 57 and irradiated from the illumination windows 37a and 37b onto the region to be observed of the subject. Then, reflected light from the region to be observed is condensed by the objective lens unit 39 and photoelectrically converted by the image pickup device 21, and a captured image signal (analog signal) of a white light image is output.

The captured image signal (analog signal) of the white light image is converted to an image signal (digital signal) by the AFE 61, input to the image processing section 63, and subjected to the digital signal process by the DSP 64. Then, a predetermined image process suitable for a normal observation image is performed in accordance with the observation mode by the normal light image processing section 72, such that normal light image data is output. The normal observation image is displayed on the display section 15 on the basis of normal light image data by the control section 65.

Next, the operation in the special light observation mode will be described.

First, an instruction of the observation mode or the like is input from the input section 17 of the endoscope apparatus 10 to the control section 65 of the processor 13, and the observation mode is set to the special light observation mode. Alternatively, the observation mode is switched from the normal light image mode to the special light observation mode. If the special light observation mode is performed, information of the observation site, such as stomach, duodenum, or small intestine, at present is designated by an operation of the input section 17. Thus, in the oxygen saturation image generation section 114 and the blood vessel depth image generation section, the color table according to the observation site is selected.

In the special light mode, three frames constitute one set, and illumination light having a different irradiation pattern is irradiated in each frame.

First, in the first frame (the frame 1 of Table 1), the narrowband light source 43a (LD405) of the narrowband light source section 43 is turned on, the narrowband light source 41a of the normal light source section 41 and the narrowband light source 43b of the narrowband light source section 43 are turned off, such that only narrowband light N2 having the wavelength of 405 nm is emitted from LD405.

In the endoscope 11, narrowband light N2 from the light source device 12 is guided to the optical deflection/diffusion members 58 of the scope tip portion 35 by the optical fibers 55b and 55c. Thus, narrowband light N2 whose light quantity is uniformized by the optical deflection/diffusion members 58 is irradiated from the illumination windows 37a and 37b onto the region to be observed of the subject.

Subsequently, an image signal of a captured image captured by the image pickup device 21 is acquired, digitalized by the AFE 61, and subjected to the digital signal process by the DSP 64 of the image processing section 63. Thus, 405 component image data is acquired and stored in the storage section 67.

Next, in the second frame (the frame 2 of Table 1), the narrowband light source 43a is turned off, the narrowband light source 41a (LD445) is turned on, and the narrowband light source 43b is maintained in the turned-off state, such that excitation light E for normal observation is emitted from LD445.

In the endoscope 11, excitation light E from the light source device 12 is guided to the fluorescent substances 57 of the scope tip portion 35 by the optical fibers 55a and 55d. Thus, excitation light E is irradiated onto the fluorescent substances 57 to emit fluorescence F, and pseudo white light BW in which excitation light E and fluorescence F are synthesized is irradiated from the illumination windows 37a and 37b onto the region to be observed of the subject.

Subsequently, an RGB image signal of a captured image captured by the image pickup device 21 is acquired, digitalized by the AFE 61, and subjected to the digital signal process by the DSP 64 of the image processing section 63. Thus, RGB image data of white light is output and stored in the storage section 67.

Subsequently, in the third frame (the frame 3 of Table 1), LD445 is turned off, the narrowband light source 43b (LD473) is turned on, and the narrowband light source 43a is maintained in the turned-off state, such that narrowband light N3 is emitted from LD473.

In the endoscope 11, as in the first frame, narrowband light N3 from the light source device 12 is guided to the scope tip portion 35 by the optical fibers 55b and 55c and irradiated from the illumination windows 37a and 37b onto the region to be observed of the subject.

Subsequently, as in the first frame, an image signal of a captured image captured by the image pickup device 21 is acquired, digitalized by the AFE 61, and subjected to the digital signal process by the DSP 64 of the image processing section 63. Thus, 473 component image data is output and stored in the storage section 67.

In the invention, the first frame and the third frame may be reversed.

In the normal light image processing section 102, RGB image data obtained in the frame 2 is read from the storage section 67, and a predetermined image process suitable for a normal observation image is performed on read RGB image data. Thus, normal light image data is output and stored in the storage section 67.

In the special light image processing section 104, spectral estimation is performed using RGB image data which is read from the storage section 67 in the spectral estimation section 106 and obtained in the second frame. Then, 445 component image data, 550 component image data, and 600 component image data are calculated and transmitted to the luminance ratio calculation section 108.

Next, in the luminance ratio calculation section 108, the blood vessel region including the blood vessel is specified from 405 component image data which is read from the storage section 67 and obtained in the second frame, and transmitted 445 component image data and 550 component image data. Subsequently, with regard to the pixels at the same position in the blood vessel region, when the luminance value of the pixel of 405 component image data is S1, the luminance value of the pixel of 445 component image data is S2, and the luminance value of the pixel of 550 component image data is S4, the luminance ratio calculation section 108 calculates the first and second luminance ratios S1/S2 and S1/S4.

In the luminance ratio calculation section 108, the blood vessel region including the blood vessel is specified from 473 component image data which is read from the storage section 67 and obtained in the third frame, and transmitted 550 component image data and 600 component image data. Subsequently, with regard to the pixels at the same position in the blood vessel region, when the luminance value of the pixel of 473 component image data is S3, the luminance value of the pixel of 550 component image data is S4, and the luminance value of the pixel of 600 component image data is S5, the luminance ratio calculation section 108 calculates the third and fourth luminance ratios S3/S4 and S5/S4.

The first and second luminance ratios S1/S2 and S1/S4 and the third and fourth luminance ratios S3/S4 and S5/S4 obtained in the above-described manner are transmitted to the oxygen saturation calculation section 112.

Subsequently, in the oxygen saturation calculation section 112, the surface layer oxygen saturation and the blood vessel depth information corresponding to the first and second luminance ratios S1/S2 and S1/S4 are calculated on the basis of the first correlation between the spectral luminance ratios S1/S2 and S1/S4 shown in FIG. 13, the surface layer oxygen saturation, and the blood vessel depth stored in the correlation storage section 110.

Subsequently, in the oxygen saturation calculation section 112, the intermediate-to-deep layer oxygen saturation and the blood volume information corresponding to the third and fourth luminance ratios S3/S4 and S5/S4 are calculated on the basis of the correlation between the spectral luminance ratios S3/S4 and S5/S4 shown in FIG. 14, the intermediate-to-deep layer oxygen saturation, and the blood volume stored in the correlation storage section 110.

Thereafter, the oxygen saturation calculation section 112 weights the surface layer oxygen saturation and the intermediate-to-deep layer oxygen saturation calculated in the above-described manner on the basis of the blood vessel depth to calculate suitable oxygen saturation according to the blood vessel depth.

The oxygen saturation, the blood vessel depth information, and the blood volume information calculated in the above-described manner are transmitted to the oxygen saturation image generation section 114.

Next, when the oxygen saturation, the blood vessel depth information, and the blood volume information have been obtained, the oxygen saturation image generation section 114 specifies the color information corresponding to the oxygen saturation on the basis of the selected color table. Then, for all pixels in the blood vessel region, the oxygen saturation, the blood vessel depth information, and the blood volume information are obtained and the color information corresponding to the oxygen saturation is specified. When the oxygen saturation and the corresponding color information have been obtained for all pixels in the blood vessel region, the oxygen saturation image generation section 114 reads normal light image data of a normal observation image serving as a reference image from the storage section 67, and reflects the color information in the normal observation image to generate oxygen saturation image data. The generated oxygen saturation image data is stored in the storage section 67.

The control section 65 reads the oxygen saturation image data from the storage section 67, and pseudo-color displays the oxygen saturation image on the display section 15 on the basis of the read oxygen saturation image data.

In the above-described manner, in the endoscope apparatus 10, it is possible to accurately calculate information regarding oxygen saturation taking into consideration the depth of the blood vessel and the blood volume while reducing the influence of the motion of the subject to reduce the influence of the depth of the blood vessel, and to display a high-definition and accurate detailed diagnostic image in which the distribution of oxygen saturation is superimposed on the normal observation image as a pseudo-color image and visualized.

Figure 15:
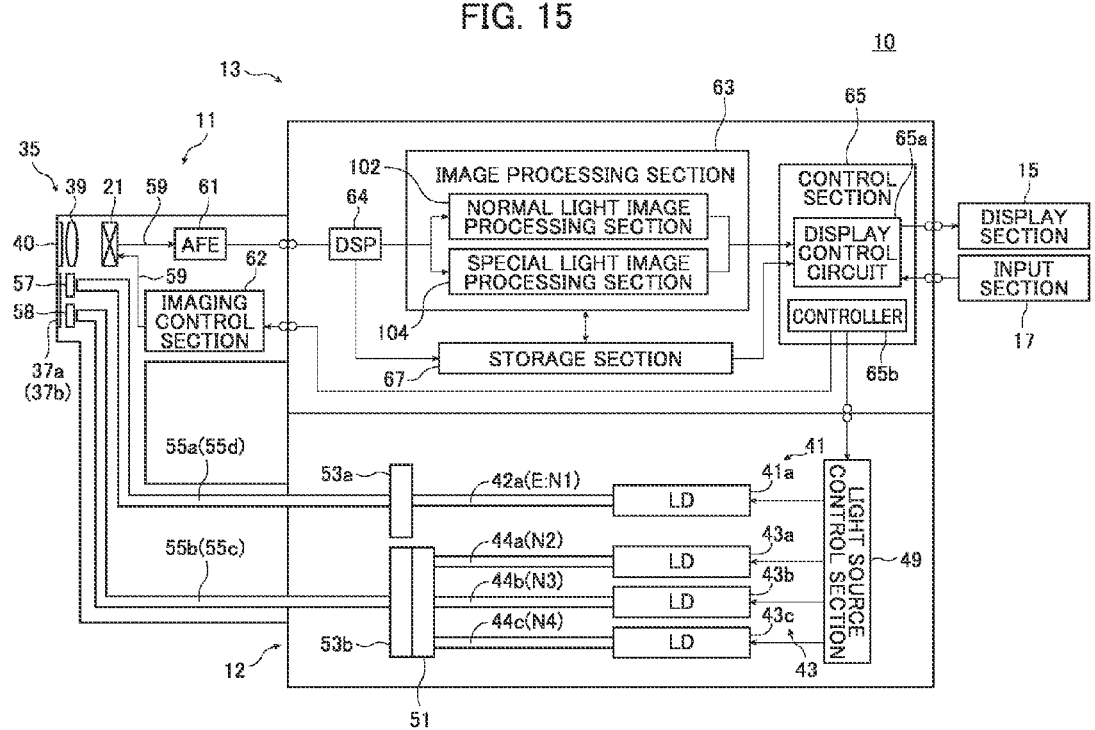
FIG. 15 is a schematic view conceptually showing the overall configuration of another example of the endoscope apparatus shown in FIG. 1.

In the above-described example, pseudo white light which is broadband light serving as standard light generated using the narrowband light source 41a of the normal light source section 41 and the fluorescent substance 57 is irradiated onto the subject to acquire the RGB image signal, thereby obtaining RGB image data for normal observation. Then, 445 component image data, 550 component image data, and 600 component image data for calculating the oxygen saturation are calculated from RGB image data by spectral estimation. However, the invention is not limited thereto, and spectral image data, such as 445 component image data, 550 component image data, 600 component image data, may not be calculated from RGB image data. For example, as shown in FIG. 15, the narrowband light source 43c (LD445) which emits narrowband light N4 having the wavelength of 445 nm as standard light may be used, and narrowband light N4 may be directly irradiated onto the subject without transmitting the fluorescent substance 57. In order to obtain another spectral image data, such as 550 component image data and 600 component image data, narrowband light having a wavelength of 550 nm, a wavelength of 600 nm, or a different wavelength may be irradiated.

In this example, it should suffice that narrowband light N4 of LD445 is set as a standard, and narrowband light N2 of LD405 and narrowband light N3 of LD473 are irradiated before and after narrowband light N4.

An endoscope apparatus shown in FIG. 15 has the same configuration as the endoscope apparatus 10 shown in FIG. 1, except that narrowband light N4 of the narrowband light source 43c is directly irradiated onto the subject, and thus description thereof will not be repeated.

Although the endoscope apparatus according to the invention has been described in detail in connection with various embodiments and examples, the invention is not limited thereto. It should be noted that various improvements or changes may be made without departing from the gist of the invention.

What is claimed is:

1. An endoscope apparatus comprising:
an illumination device configured to irradiate at least three kinds of illumination light having different wavelengths including standard light, first reference light, and second reference light onto a biological object serving as a subject;
an illumination light switching device configured to periodically switch the at least three kinds of illumination light irradiated by the illumination device in each imaging frame;
an imaging device configured to receive return light from the subject onto which the at least three kinds of illumination light switched by the illumination light switching device are irradiated and capture image data in each imaging frame; and
a biological information acquisition device configured to acquire biological function information relating to the biological object from the captured image data captured by the imaging device,
wherein the illumination light switching device switches an irradiation order of the at least three kinds of illumination light by the illumination device at least in order of the first reference light, the standard light, and the second reference light in the same cycle, and
the imaging device acquires at least the image data of a first reference image, the image data of a standard image, and the image data of a second reference image in the same cycle using the respective return light of the at least three kinds of illumination light which are irradiated onto the biological object by the illumination device at least in order of the first reference light, the standard light, and the second reference light in the same cycle, and acquires at least the first reference image, the standard image, and the second reference image, respectively, and
the standard light is broadband light including a visible light wavelength band, and the first reference light and the second reference light are narrowband light having a predetermined wavelength bandwidth, and
the biological information acquisition device
performs a spectral estimation process using captured image data obtained by irradiation of the broadband light,
obtains, as the standard image, a first standard wavelength image for comparison with the first reference image captured in the same cycle as the standard image by the first reference light and a second standard wavelength image for comparison with the second reference image captured in the same cycle as the standard image by the second reference light, and
calculates the biological function information based on the first reference image and the first standard wavelength image, and/or the second reference image and the second standard wavelength image.

2. The endoscope apparatus according to claim 1, wherein the imaging device is an RGB color image sensor.

3. The endoscope apparatus according to claim 2, wherein the broadband light is pseudo white light including excitation light which is narrowband light having a predetermined wavelength and fluorescence which is generated from a fluorescent substance excited by the excitation light, and
a wavelength of the excitation light falls between a wavelength of the first reference light and a wavelength of the second reference light.

4. The endoscope apparatus according to claim 3, wherein the illumination device includes three narrowband light sources which respectively emit the excitation light, the first reference light, and the second reference light, and
a narrowband light source which emits the excitation light and the fluorescent substance constitute a broadband light source which emits the broadband light.

5. The endoscope apparatus according to claim 1, wherein each of the standard light, the first reference light, and the second reference light is narrowband light having a predetermined wavelength bandwidth, and a wavelength of the standard light falls between a wavelength of the first reference light and a wavelength of the second reference light, and
the biological information acquisition device calculates the biological function information based on the standard image by the standard light, the first reference image by the first reference light, and the second reference image by the second reference light.

6. The endoscope apparatus according to claim 2, wherein the illumination device further includes a broadband light source which emits broadband light including a visible wavelength band, in addition to three narrowband light sources which respectively emit the standard light, the first reference light, and the second reference light.

7. The endoscope apparatus according to claim 4, further comprising:
a display device configured to display the biological function information; and
a normal observed image acquisition device configured to irradiate the broadband light emitted from the broadband light source onto the biological object to acquire a normal observed image by the imaging device,
wherein the display device displays a biological function information image in which the biological function information calculated by the biological information acquisition device is overlaid on the normal observed image acquired by the normal observed image acquisition device.

8. The endoscope apparatus according to claim 4, wherein the narrowband light source which emits narrowband light as the standard light or the excitation light is a first blue laser which emits narrowband light having a wavelength in a blue region, the narrowband light source which emits narrowband light as the first reference light is a second blue laser which emits narrowband light in a wavelength band from the blue region to a blue-green region longer than the emission wavelength band of the first blue laser, and the narrowband light source which emits narrowband light as the first reference light is a third blue laser which emits narrowband light in a wavelength band from a blue-violet region to a blue region having a wavelength shorter than the emission wavelength band of the first blue laser.

9. The endoscope apparatus according to claims 4, wherein the wavelength band of narrowband light as the standard light or the excitation light is 440±10 nm, the wavelength band of narrowband light as the first reference light is 470±10 nm, and the wavelength band of narrowband light as the second reference light is 400±10 nm.

10. The endoscope apparatus according to claim 1, wherein the biological function information is information relating to components of the biological object and a structure of the biological object, and the biological information acquisition device separates and images information relating to the components of the biological object and information relating to the structure of the biological object based on a first feature quantity obtained by comparing a first reference image by the first reference light with the standard image by the standard light and a second feature quantity obtained by comparing a second reference image by the second reference light with the standard image.

11. The endoscope apparatus according to claim 1, wherein the first reference light is narrowband light having a wavelength suitable for acquiring oxygen saturation of blood of the biological object as information relating to the components of the biological object, and the second reference light is narrowband light having a wavelength suitable for acquiring information of a surface layer blood vessel of the biological object as information relating to the structure of the biological object.

12. The endoscope apparatus according to claim 1, wherein the biological information acquisition device computes oxygen saturation of blood of the biological object as information relating to components of the biological object and computes blood vessel depth and/or blood volume of the biological object as information relating to structure of the biological object.

13. The endoscope apparatus according to claim 1, wherein the imaging device is a color image pickup device capable of separately imaging at least three wavelength bands.

14. The endoscope apparatus according to claim 1, wherein the standard light and the first and second reference light are emitted from different illumination openings at a tip of the endoscope and illuminate the biological object.

15. The endoscope apparatus according to claim 1, wherein the illumination light switching device switches the irradiation order of the illumination light such that the standard light is in the middle of the irradiation order, when the at least three kinds of illumination light having the different wavelengths including the standard light, the first reference light, and the second reference light are irradiated onto the biological object serving as the subject by the illumination device.

16. The endoscope apparatus according to claim 1, wherein the biological information acquisition device calculates the biological function information based on the first reference image and the first standard wavelength image, and the second reference image and the second standard wavelength image, and the biological function information is information relating to components of the biological object and a structure of the biological object.

* * * * *